US009622853B2

(12) United States Patent
Argal et al.

(10) Patent No.: US 9,622,853 B2
(45) Date of Patent: *Apr. 18, 2017

(54) POLYMERIC COMPOSITION FOR OCULAR DEVICES

(75) Inventors: Sanjay Ram Swaroop Argal, Vadodara (IN); Munavvar Tahir Hussain, Vadodara (IN); Vinod Chintamani Malshe, Mulund (East) Mumbai (IN); Abhijit Bhagvat Patil, Navi Mumbai (IN)

(73) Assignee: Jagrat Natavar Dave, Vadodara (IN)

( * ) Notice: Subject to any disclaimer, the term of this patent is extended or adjusted under 35 U.S.C. 154(b) by 229 days.

This patent is subject to a terminal disclaimer.

(21) Appl. No.: 13/808,614

(22) PCT Filed: Jul. 5, 2011

(86) PCT No.: PCT/IB2011/052976
§ 371 (c)(1),
(2), (4) Date: Jan. 7, 2013

(87) PCT Pub. No.: WO2012/004744
PCT Pub. Date: Jan. 12, 2012

(65) Prior Publication Data
US 2013/0109779 A1    May 2, 2013

(51) Int. Cl.
*C08F 220/12* (2006.01)
*A61F 2/14* (2006.01)
*A61F 2/16* (2006.01)
*A61L 27/26* (2006.01)
*C08F 220/18* (2006.01)
*C08F 220/30* (2006.01)
*C08K 5/00* (2006.01)
*C08L 33/14* (2006.01)
*G02B 1/04* (2006.01)
*G02C 7/02* (2006.01)
*G02C 7/04* (2006.01)
*G02C 7/06* (2006.01)
*C08F 222/10* (2006.01)
*C08F 220/28* (2006.01)
*C08K 5/13* (2006.01)

(52) U.S. Cl.
CPC ............ *A61F 2/1613* (2013.01); *A61F 2/16* (2013.01); *A61F 2/1624* (2013.01); *A61L 27/26* (2013.01); *C08F 220/18* (2013.01); *C08F 220/30* (2013.01); *C08K 5/005* (2013.01); *C08L 33/14* (2013.01); *G02B 1/043* (2013.01); *G02C 7/022* (2013.01); *G02C 7/041* (2013.01); *G02C 7/049* (2013.01); *G02C 7/06* (2013.01); *A61F 2230/0006* (2013.01); *A61L 2430/16* (2013.01); *C08F 222/1006* (2013.01); *C08F 2220/281* (2013.01); *C08K 5/13* (2013.01); *G02C 2202/20* (2013.01)

(58) Field of Classification Search
CPC ........ C08F 220/18; C08F 220/30; A61F 2/14; A61F 2/16; A61F 2/168
See application file for complete search history.

(56) References Cited

U.S. PATENT DOCUMENTS

| | | | |
|---|---|---|---|
| 5,359,021 A | 10/1994 | Weinschenk, III et al. | |
| 5,470,932 A | 11/1995 | Jinkerson | |
| 2006/0000287 A1 | 1/2006 | Arai et al. | |
| 2006/0110428 A1 | 5/2006 | DeJuan et al. | |
| 2011/0245442 A1* | 10/2011 | Terrisse | 526/227 |
| 2013/0107201 A1 | 5/2013 | Argal et al. | |
| 2016/0220348 A1 | 8/2016 | Argal et al. | |

FOREIGN PATENT DOCUMENTS

| | | | |
|---|---|---|---|
| EP | 0485197 | | 5/1992 |
| EP | 485197 A | * | 5/1992 |
| EP | 2045648 | | 4/2009 |
| FR | 2930731 | | 11/2009 |
| JP | 06-007424 | | 1/1994 |
| JP | 06007424 A | * | 1/1994 |
| JP | 11-343234 | | 12/1999 |
| WO | WO 2006/047698 | | 5/2006 |
| WO | WO 2010/046240 | | 4/2010 |
| WO | WO 2010/070664 | | 6/2010 |
| WO | WO 2012/004744 | | 1/2012 |
| WO | WO 2012/004746 | | 1/2012 |

OTHER PUBLICATIONS

Machine Translation of JO 06-007424A; Kanebako et al; Jan. 1994.*
Communication Pursuant to Article 94(3) EPC Dated Oct. 2, 2014 From the European Patent Office Re. Application No. 11748721.5.
Communication Pursuant to Article 94(3) EPC Dated Sep. 29, 2014 From the European Patent Office Re. Application No. 11748722.3.
Communication Relating to Results of the Partial International Search Dated Dec. 16, 2011 From the International Searching Authority Re. Application No. PCT/IB2011/052976.
Communication Relating to Results of the Partial International Search Dated Dec. 16, 2011 From the International Searching Authority Re. Application No. PCT/IB2011/052978.
International Search Report and the Written Opinion Dated Feb. 20, 2012 From the International Searching Authority Re. Application No. PCT/IB2011/052976.

(Continued)

*Primary Examiner* — Karuna P Reddy

(57) ABSTRACT

Polymeric and co-polymeric compositions useful for preparing ophthalmic and ocular devices, such as implantable intraocular lenses (IOL) and contact lenses, and processes of forming the compositions and devices are provided. The disclosed polymeric or co-polymeric composition may include a curcuminoid compound as a UV-blocker, and is derived from a pre-polymerization mixture of monomers which comprises at least 50 weight percents acrylate monomers and exhibiting visible light transparency and ultraviolet light opacity. The disclosed co-polymeric composition may alternatively, or in addition, be derived from a pre-polymerization mixture of defined monomers.

27 Claims, 6 Drawing Sheets

(56) References Cited

OTHER PUBLICATIONS

International Search Report and the Written Opinion Dated Feb. 20, 2012 From the International Searching Authority Re. Application No. PCT/IB2011/052978.
Ishikawa et al. Database WPI, XP002664738, Week 199410, AN 1994-077184, 1994. Abstract & JP 06-007424.
International Preliminary Report on Patentability Dated Jan. 17, 2013 From the International Bureau of WIPO Re. Application No. PCT/IB2011/052978.
Communication Pursuant to Article 94(3) EPC Dated Jan. 28, 2014 From the European Patent Office Re. Application No. 11748721.5.
Communication Pursuant to Article 94(3) EPC Dated Jan. 28, 2014 From the European Patent Office Re. Application No. 11748722.3.
International Preliminary Report of Patentability Dated Jan. 17, 2013 From the International Bureau of WIPO Re. Application No. PCT/IB2011/052976.
Official Action Dated Mar. 30, 2015 From the US Patent and Trademark Office Re. U.S. Appl. No. 13/808,624.
Communication Pursuant to Article 94(3) EPC Dated Sep. 15, 2015 From the European Patent Office Re. Application No. 11748721.5.
Official Action Dated Oct. 26, 2015 From the US Patent and Trademark Office Re. U.S. Appl. No. 13/808,624.
Examination Report Under Sections 12 & 13 of the Patents Act, 1970 and the Patents Rules, 2003 Dated Jan. 23, 2017 From the Government of India, Patent Office, Intellectual Property Office Re. Application No. 2888/MUM/2010. (8 Pages).

* cited by examiner

POLYMERIC COMPOSITION FOR OCULAR DEVICES

RELATED APPLICATIONS

This application is a National Phase of PCT Patent Application No. PCT/IB2011/052976 having International filing date of Jul. 5, 2011, which claims the benefit of India Patent Application Nos. 1938/MUM/2010 filed on Jul. 5, 2010, 2888/MUM/2010 filed on Oct. 18, 2010 and 273/MUM/2011 filed on Feb. 1, 2011. The contents of the above applications are all incorporated by reference as if fully set forth herein in their entirety.

FIELD AND BACKGROUND OF THE INVENTION

The present invention, in some embodiments thereof, relates to polymeric and co-polymeric materials, and more particularly, but not exclusively, to polymeric and co-polymeric materials useful for preparing ocular devices such as intraocular, ophthalmic implants and contact lenses.

Light is an electromagnetic wave emitted by excited electrons; and as such can reflect, refract and diffract. The human eye is a complex anatomical device, which evolved to interact with light and facilitates interpretation of shapes, colors, dimensions and relative position of objects by processing the light they reflect or emit. Similarly to a camera, the eye is able to refract light and produce a focused image that can stimulate neural responses and provide the ability to see. The iris regulates the amount of light admitted to the interior of the eye, the cornea and the lens focus the light rays from an object being viewed onto the retina which transmits the image of the object to the brain via the optic nerve. About 75% of the focusing is provided by the cornea, with the other 25% provided by the crystalline lens which may acquire variable focal lengths.

The cornea is the most anterior structure of the eye. Since it has to be transparent to allow light to enter the eye, there are no blood vessels in the cornea. The cornea is composed of collagen fibers packed together in an organized pattern, thereby providing the cornea its light transparent nature. The cornea has the highest concentration of nerve endings in the entire body, thus making it extremely sensitive to any kind of trauma. The front view of the cornea is of an aspheric shape, where the vertical dimension is smaller than the horizontal dimension by about 1-2%. The anterior is typically about 11.7 mm in diameter.

The quality of vision depends on many factors including the size and shape of the eye, and the transparency of the cornea and lens. When age or disease causes the lens to become less transparent, vision deteriorates because of the diminished light which can be transmitted to the retina. This deficiency in the lens of the eye is medically known as a cataract. An accepted treatment for this condition is a surgical replacement of the lens.

Corrective optic devices are used to correct refractive errors of the eye by modifying the effective focal length of the lens in order to alleviate the effects of conditions such as nearsightedness (myopia), farsightedness (hyperopia) or astigmatism. Another common condition in older patients is presbyopia which is caused by the eye's crystalline lens losing transparency (cataract) and/or elasticity, progressively reducing the ability of the lens to accommodate, namely to focus on objects close to the eye.

Corrective optic devices, also referred to herein as ophthalmic devices, include, for example, contact lenses and IOLs (intraocular lens, an implanted lens in the eye, usually replacing the existing crystalline lens because it has been clouded over by a cataract, or as a form of refractive surgery to change the eye's optical power), keratoprostheses, corneal rings, phakic lenses, aphakic lenses, capsular bag extension rings, corneal inlays and corneal onlays. Corrective optic devices for refractive errors also include eyeglasses, sunglasses or spectacles, comprising frames bearing lenses which are worn in front of the eyes normally for vision correction, eye protection, or for protection from UV rays.

Ophthalmic devices include cornea implants for artificial keratoplasty (keratoprostheses), cornea onlay lenses (contact lenses) or corneal inlay lenses or rings for correcting refractive errors, intraocular lenses for cataract surgery, phakic intraocular lenses in the posterior chamber of eye and lenses for optical instruments. Generally, such devices operate accordion to the refraction and/or diffraction principles stemming from their shape and composition.

Contact lens is a corrective, cosmetic, or therapeutic lens usually placed on and in contact with the cornea of the eye, hence the name contact lens. Contact lenses usually serve the same corrective purpose as eyeglasses, but are typically soft, lightweight and virtually invisible (some commercial lenses are tinted a faint blue to make them more visible when immersed in cleaning and storage solutions). Some cosmetic lenses are deliberately colored to alter the appearance of the eye. Some contact lenses have a thin surface treatment which is a UV-absorbing coating; this helps to reduce UV damage to the eye's natural lens. It has been estimated that 125 million people use contact lenses worldwide (2%).

Ophthalmic implants (also referred to herein as implantable ophthalmic devices), such as intraocular lenses, differ from contact lenses mainly by their permanent placement in the eye. Intraocular lenses (IOL), also known as implantable contact lenses, are special small corrective lenses surgically implanted in the eye's posterior chamber behind the iris and in front of the lens to correct higher degrees of myopia and hyperopia. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an intraocular lens. Implantable ophthalmic devices can be surgically implanted into a living cornea, or in other cases, are located in proximity to a damaged living cornea. It is highly desirable, even essential, for the long term viability of such corrective lens structure onlays or implants, that the material constituting these devices be chemically and physically stable and capable of sustaining and possible filtering damaging radiation. Typically, this material is a polymer or co-polymer of some sort.

Over the years, numerous types of IOLs have been developed for correcting vision deficiencies. Generally, such lenses operate accordion to one or two basic optical principles: refraction and diffraction.

A typical optical device is manufactured from a polymeric composition, has a diameter of about 5-7 mm, and is supported in the eye by the spring force of flexible loops called haptics.

In general, the material used for ophthalmic implants is required to be and to remain stable in prolong exposure to wear and UV light, and remain transparent and substantially glistening-free and vacuoles-free for extended periods of time at the physiological conditions of the eye, namely in contact with the eye's living tissue, tear enzymes and 37° C. A typical IOL is manufactured from polymethyl methacrylate, has a diameter of about 5-7 mm, and is supported in the eye by the spring force of flexible loops called haptics. Other materials are also used, and there are a variety of lens style and haptic designs.

Most contemporary contact optical devices, such as contact lenses and ophthalmic implants which are used for small incision cataract surgery, require foldable materials like hydrophilic and hydrophobic acrylics and silicones; however, hydrophilic acrylic/hydrogel suffers with incompatibly low refractive index (RI) and high posterior capsular opacification (PCO) rate. Other mechanical characteristics also contribute to this incompatibility, such as the springiness of silicon-based materials, which may result in corneal endothelium damage and/or rupture of capsular bag. Polymeric compositions such as hydrophobic acrylics are more desirable as these are typically characterized by higher RI allowing smaller incision cataract surgery, minimal chances of PCO and controlled elasticity.

Thus, ophthalmic devices made from polymeric compositions should be transparent, flexible, deformable, glistening-free, vacuoles-free, contaminant-free (leachables), have low tackiness, low internal reflections, characterized by low stress generation or local burning while machining, and other handling and manufacturing problems.

WO 1994/011764 teaches foldable intraocular lenses made from polymeric compositions of high refractive index, comprising a copolymer including a first constituent derived from a first monomeric component the homopolymers of which have a refractive index of at least about 1.50, a second constituent derived from a second monomeric component other than the first monomeric component the homopolymers of which have a glass transition temperature of less than about 30° C., a third constituent derived from a crosslinking monomeric component in an amount effective to facilitate returning a deformed intraocular lens made of these compositions to its original shape, and a fourth constituent as a hydrophilic monomer. However WO 1994/011764 is silent with respect to the superfluous unreacted monomer content which ultimately affects glistening property of the lens and amount of undesired leachable (extractable) impurities.

WO 1999/007756 discloses high refractive index copolymer compositions suitable for use in ophthalmic lenses, such as foldable intraocular lenses, consisting of conventional aromatic monomer and diacrylate oligomers such as epoxy acrylate, acrylated acrylics. WO 1999/007756 is silent with respect to several factors such as tackiness (stickiness, adhesiveness) of the resulting lenses resulting from monomers having a low Tg, internal reflection resulting from monomers having a high RI, and manufacturing process related internal stresses which results in non-linear heterogeneous mechanical/optical behavior of lenses.

U.S. Pat. No. 7,585,900 discloses soft, high refractive index, acrylic materials (polyethyl/methacrylate, PEA/PEMA) useful as intraocular lens materials, containing an aryl acrylic hydrophobic monomer as the single principal device-forming monomer and a tack-reducing macromer additive (diacrylated polydimethyl siloxane, PDMS). However, PDMS requires custom complex syntheses leading to higher production costs.

U.S. Pat. No. 5,331,073 discloses high refractive index polymeric compositions and foldable intraocular lenses made from such compositions. However, these acrylic-based polymeric compositions include fluorine-containing monomers to rectify tackiness, which are costly and present some biocompatibility issues.

U.S. Pat. No. 5,674,960 discloses PEA/PEMA-based high refractive index polymeric compositions, however, these compositions result in devices that suffer from internal reflection and persistent vacuoles in the ophthalmic implants made therefrom.

EP 1030194 discloses polymeric compositions for soft, transparent and flexible intraocular lens, based on combinations of aryl acrylate and hydrophilic monomer, wherein the content of the hydroxyalkyl acrylate monomer is at least 50%, rendering it too hydrophilic for compatible contact or implantable lenses.

U.S. Pat. No. 6,653,422 discloses soft, high refractive index, polymeric compositions for soft intraocular lenses, having an elongation of at least 150%, constituting of aromatic monomers such as 4-phenyl butyl acrylate, 3-benzyloxypropyl methacrylate in addition to PEA/PEMA.

U.S. Pat. No. 5,693,095 discloses polymeric compositions for foldable ophthalmic lenses, comprising hydrophilic and hydrophobic aromatic acrylic component.

U.S. Patent Application Publication No. 2008139769 discloses (meth)acrylate copolymer compositions for soft intraocular lenses, obtained by copolymerization of a monomer mixture containing aromatic acrylic hydrophilic components along with hydrophobic components.

WO 2004/029675 teaches the formation of intraocular lenses through a process of pre-gel formation and in fused silica mold and a process of casting and extraction.

U.S. Pat. No. 7,304,117 teaches diphenyl azo-based reactive yellow dyes and a process for preparing polymers using the same in the manufacturing of ophthalmic devices, such as intraocular lenses, having blue light absorption properties. Said polymers are capable of blocking blue light from reaching the retina of an eye implanted with the ophthalmic device, and thereby preventing potential damage to the retina.

U.S. Pat. No. 5,433,746 discloses polymer composition constituting aromatic monomers like PEA/PEMA and the likes.

Implantable ophthalmic devices must overcome such issues as cytotoxicity and biocompatibility, which may arise from leachable (extractible) contaminants, hence all ophthalmic devices should be free from leachable contaminants. To reduce these preexisting impurities, extraction steps are typically carried out. WO 2004/029675, U.S. Patent Application Publication Nos. 2005258096, 2004031275 and 2003116873 disclose such extraction methods; however, such batch extraction methods suffer from various process complexities and solvent issue.

U.S. Pat. No. 5,603,774 teaches reduction of the tackiness associated with certain such soft acrylic polymers useful for foldable intraocular lenses (IOLs), by plasma treatment of the polymer surface.

Additional background art includes U.S. Pat. Nos. 7,585,900, 5,693,095, 5,290,892, 5,403,901, 5,433,746, 5,674,960, 5,716,403, 5,861,031, 4,304,895 and 4,528,311, U.S. Patent Application Publication Nos. 2003130460, 2009132039, 2008269884, 2003130460, 2008139769, 2008021129, 2001014824, 2003116873 and 2005258096, WO 2001/018079, WO 2006/210438, WO 2006/187042, WO 1999/07756, WO 2009/137525, WO 2009/120511, WO 20008/011566, WO 2008/011564, WO 2001/018079, WO 2001/018078, WO 1999/007756, WO 2004/11764, WO 2004/029675, WO 2004/031275, WO 2009/104516, WO 2006/095750, WO 2009/025399, JP 2003119226, KR 20090047478, EP 1857477, CN101137684.

Light and oxygen induce degradation reactions in polymer-based devices that may not only modify them visually but also exert a detrimental influence on numerous mechanical, physical and optical properties. Such adverse effects can be minimized by use of light stabilizers which are chemical compounds able to interface with the physical and chemical process of light induced degradation.

Radiation reaching the surface of the earth is composed of direct sunlight and scattered light, and the ultraviolet (UV) part of the radiation spectrum is the part that is considered responsible for polymer degradation. The Environmental Protection Agency (EPA or USEPA) designates sub-ranges of ultraviolet light as UVA (315-400 nm), UVB (280-315 nm) and UVC (10-280 nm). UVC and partly UVB rays are absorbed in the oxygen and ozone containing layer located in stratosphere, therefore only part of UVB and UVA radiation reaches the surface of the earth, and constitutes the main factor in aging for polymer-based systems. However, thinning of ozone layer is shifting UV spectral composition towards shorter wavelengths. It is accepted that UV radiation in the range of 280-380 nm, which corresponds to 420-320 kJ, is responsible for polymer degradation. This energy is sufficient to break C—C, C—H, C—O, C—Cl, C—N covalent bonds, hence signifies the need of using light stabilizers in ophthalmic devices which are exposed to direct or indirect sun-light.

UV light is also damaging to living cells, and among these, cell that enable vision. Visible violet light contributes only 5% to scotopic vision (the monochromatic vision of the eye in dim light) but it is responsible for up to 14% UV blue phototoxicity (a phenomenon known in live-cell, where illuminating a fluorescent molecule or a fluorophore, causes the selective death of the cells that express this fluorophore). Ultraviolet radiation may also contribute to the development of ocular disorders such as cataract, ocular cancers, photokeratitis, macular degeneration and corneal degenerative changes (e.g. pterygium, droplet climatic keratopathy, pinguecula), retinitis pigmentosa, night blindness, cystoid macular oedema, solar retinopathy (damage to the eye's retina, particularly the macula, from prolonged exposure to solar radiation), ocular melanomas and like damages.

Photokeratitis (also known as welder's flash or arc eye) is an inflammation of the cornea caused by a brief exposure to UV radiation. Like sunburn, it may be painful and may create symptoms including red eyes, a foreign body sensation or gritty feeling in the eyes, extreme sensitivity to light and excessive tearing. Scientific studies and research growing out of the U.S. space program have shown that exposure to small amounts of UV radiation over a period of many years may increase the chance of developing a cataract, and may cause damage to the retina, the nerve-rich lining of the eye that is used for seeing. Retina damage is usually not reversible, and cumulative damage of repeated exposure may contribute to chronic eye disease, as well as increase the risk of developing skin cancer around the eyelids. Long-term exposure to UV light is also a risk factor in the development of pterygium (a growth that invades the corner of the eyes) and pinguecula (a yellowish, slightly raised lesion that forms on the surface tissue of the white part of the eye).

Ultraviolet light (higher energy with respect to visible light) can be damaging to the light receptor cells. With a few exceptions (e.g., snakes, placental mammals), most organisms avoid these effects by having absorbent oil droplets around their cone cells. The alternative, developed by organisms that had lost these oil droplets in the course of evolution, is to make the lens impervious to UV light, precluding the possibility of UV light being detected, as it does not reach the retina. In the human and other animal eye, UV light is absorbed by molecules known as chromophores, which are present in the eye cells and tissues. Chromophores absorb light energy from the various wavelengths at different rates; a pattern known as absorption spectrum. Furthermore, natural chromophores found in the eye block UV light by fluorescence.

Transparent polymer-based ophthalmic devices are most sensitive to UV light, including visible violet light (400-440 nm). Most of the ophthalmic device research and manufacturing companies incorporate synthetic UV-blockers/absorbers (also referred to herein as light stabilizing additives or light stabilizers) in their ophthalmic devices. The primary function of light stabilizers is to protect the substance from the long-term degradation effects from light, most frequently ultraviolet light. Different UV stabilizers are utilized depending upon the substrate, intended functional life, and sensitivity to UV degradation. UV stabilizers, such as hydroxyphenyl-benzotriazole, hydroxyphenyl-triazine and benzophenone-based light stabilizers, act by absorbing the UV radiation and preventing the formation of, or scavenging, free radicals. Depending upon substitution, the UV absorption spectrum is changed to match the application, while their concentrations typically range from 0.05% to 5% by weight of the polymer.

Unlike naturally occurring chromophores, synthetic dyes used as UV-blockers for incorporation in transparent polymer-based ophthalmic devices typically do not show any kind of fluorescence, hence are less effective in blocking UV radiation than naturally occurring UV-blockers. Furthermore, synthesis of organic UV-blockers/absorbers intended for incorporation into transparent polymer-based ophthalmic devices involves complex, multi-step and costly manufacturing process, which limits the choice of the polymer to great extent. In addition to their production limits, synthetic light stabilizing additives may lack biocompatibility to some extent, and as such may cause the development of hypersensitivity of the epithelium cell layers after prolonged contact therewith, and may cause impairment of scotopic vision.

Moreover, in the case of implantable ophthalmic devices, the thickness of a typical device is required to be kept at a minimum for the sake of smaller incisions. In addition, the concentration of any potentially harmful UV-blockers must be kept at the lowest. Thus, since there is a direct link between the UV-blocking effect and the amount of UV-blocker in the path of the light, UV-blockers are required to have a large cross-section for interaction with the incoming UV radiation. UV-blockers with a relatively low cross-section are less suitable for use in transparent polymer-based ophthalmic devices since they require a long light-path and/or a high concentration in the transparent polymer-based ophthalmic device in order to block UV effectively.

U.S. Pat. Nos. 5,234,990 and 5,578,676 teach compositions for forming anti-reflective layers for DUV microlithographic processes, which include polysulfone and polyurea polymers that possess inherent light absorbing properties at deep ultraviolet wavelengths. These compositions are applied to a substrate to form an anti-reflective coating, and thereafter a photoresist material that is compatible with the anti-reflective coating is applied. These polymers are said to include an additive such as 4,4,-bis(N,N-dimethylamino) benzophenone, 7-diethylamino-4-methylcoumarian, curcumin, 3-aminopropyltriethoxysilane or (3-glycidoxypropyl)trimethoxysilane. These polymers are also said to be opaque, hence are not suitable for use in ophthalmic devices.

U.S. Pat. No. 7,304,117 teaches novel azo-based reactive yellow dyes and a process for manufacturing polymers, using the same in the manufacturing of ophthalmic devices, such as intraocular lenses, having blue light absorption properties. Said polymers are capable of blocking blue light from reaching the retina of an eye implanted with the ophthalmic device, and thereby preventing potential damage to the retina.

U.S. Patent Application Publication No. 20070204412 teaches transparent silicone polymers and elastomers colored by curcumin and/or a derivative thereof.

SUMMARY OF THE INVENTION

The present invention, in some embodiments thereof, relates to polymeric and/or co-polymeric compositions useful for forming intraocular, ophthalmic implants, contact lenses and other ophthalmic and ocular devices.

The present inventors have devised the following compositions:

i) an improved hydrophobic co-polymeric composition made from a unique combination of constituents which confer a unique combination of beneficial optical, chemical and mechanical attributes;

ii) a polymeric or co-polymeric composition, based on at least 50 weight percents acrylate monomers, which includes a curcuminoid compound that serves as a natural and highly effective UV-blocker; and iii) the improved hydrophobic co-polymeric composition described in (i) above, further comprising a curcuminoid compound as a UV-blocker.

Hence, according to an aspect of some embodiments of the present invention, there is provided a co-polymeric composition which includes a polymeric backbone composed of a plurality of backbone units covalently linked to one another, the backbone units being derived from a pre-polymerization mixture of monomers which includes:

a first aromatic acrylate monomer, characterized as forming a first homopolymer having a refractive index that ranges from 1.50 to 1.53;

a second aromatic acrylate monomer, characterized as forming a second homopolymer having a Tg lower by a range of 2° C. to 30° C. than a Tg of the first homopolymer;

a third monomer, characterized as forming a third homopolymer having a Tg lower than 35° C.;

a fourth monomer, characterized as forming a fourth homopolymer which is capable of absorbing water to at least 20% of the total weight of the fourth homopolymer; and a fifth monomer, being a crosslinking monomer, wherein:

a concentration of the first aromatic acrylate monomer ranges from 50% to 60% of the total weight of the composition;

a concentration of the second aromatic acrylate monomer ranges from 15% to 20% of the total weight of the composition;

a concentration of the third monomer ranges from 10% to 15% of the total weight of the composition;

a concentration of the fourth monomer ranges from 5% to 10% of the total weight of the composition;

a concentration of the fifth monomer ranges from 2% to 5% of the total weight of the composition; and the composition being formulated for ophthalmic application.

In some embodiments, the hydrophobic co-polymeric composition presented herein further includes an ultraviolet absorbing compound.

In some embodiments, the hydrophobic co-polymeric composition further includes at least one curcuminoid compound incorporated therein or thereon.

In some embodiments, a concentration of the first aromatic acrylate monomer ranges from 52% to 59% of the total weight of the composition; the concentration of the second aromatic acrylate monomer ranges from 15% to 19% of the total weight of the composition; the concentration of the third monomer ranges from 11% to 15% of the total weight of the composition; the concentration of the fourth monomer ranges from 7% to 9% of the total weight of the composition; and the concentration of the fifth monomer ranges from 2% to 3.5% of the total weight of the composition.

In some embodiments, the first aromatic monomer is selected from the group consisting of 2-phenoxyethyl acrylate, 2-phenoxy ethyl methacrylate, 2-benzyloxy ethyl acrylate, 2-benzyloxy ethyl methacrylate and combinations thereof.

In some embodiments, the second aromatic monomer is selected from the group consisting of 2-phenylethyl acrylate, benzyl acrylate, cyclohexyl acrylate, 2-chlorophenyl acrylate, 4-methyl benzyl acrylate, 2,4,6-tribromophenyl acrylate, pentabromophenyl acrylate and any combinations thereof.

In some embodiments, the third monomer is selected from the group consisting of cellosolve methacrylate, methoxy ethyl acrylate, polyethylene glycol monomethacrylate, 1-dihydroxyperfluorobutyl methacrylate, 2,5-dibromopropyl methacrylate, hexyl methacrylate, glycerol monomethacrylate, trifluoroethyl methacrylate, butyl methacrylate, n-ocyl/isooctyl methacrylate, n-decyl/isodecyl methacrylate, ethyl methacrylate, ethylene triglycol methacrylate, butyl diglycol methacrylate, methoxy polyethylene glycol 350 methhacrylate, methoxy polyethylene glycol 500 methhacrylate, methoxy polyethylene glycol 1000 methhacrylate, methoxy polyethylene glycol 2000 methhacrylate. methoxy polyethylene glycol 5000 methhacrylate, polypropylene glycon methacrylate, ethoxytriglycol methacrylate, 2-ethoxyethoxy ethyl methacrylate, methoxy triethyleglycol methacrylate, phenoxy polyethylene glycol monomethacrylate and any combinations thereof.

In some embodiments, the forth monomer is selected from the group consisting of hydroxylethyl methacrylate, glycerol monomethacrylate, ethylene triglycol methacrylate, butyl diglycol methacrylate, methoxy polyethylene glycol 350 methhacrylate, methoxy polyethylene glycol 500 methhacrylate, methoxy polyethylene glycol 1000 methhacrylate, methoxy polyethylene glycol 2000 methhacrylate, methoxy polyethylene glycol 5000 methhacrylate, polypropylene glycon methacrylate, ethoxytriglycol methacrylate, methoxy triethyleglycol methacrylate, phenoxy polyethylene glycol monomethacrylate and any combinations thereof.

In some embodiments, the fifth monomer is selected from the group consisting of ethylene glycol dimethacrylate, 1,4-butane diol diacrylate, glycerol dimethacrylate, allyl methacrylate, 1,6 hexane diol diacrylate, 1,4-butanediol dimethacrylate, 1,6-hexane diol dimethacrylate and any combinations thereof.

In some embodiments, the mixture further includes a free radical polymerization initiator.

In some embodiments, the initiator is a low temperature dissociation initiator.

In some embodiments, the initiator is selected from the group consisting of dicetyl peroxydicarbonate, tert-butyl peroxypivalate, diisobutyryl peroxide, dimyristyl peroxydicarbonate, 1,1,3,3-tetramethylbutyl peroxypivalate, tert-butyl peroxyneoheptanoate, di(2-neodecanoylperoxy-isopropyl)benzene, cumylperoxy-neodecanoate, 1,1,3,3-tetramethylbutylperoxy-neodecanoate, t-butylperoxy-neodecanoate, t-butylperoxy-neoheptanoate and any combinations thereof.

In some embodiments, the ultraviolet absorbing compound is selected from the group consisting of a benzophenone, 2-hydroxybenzophenone, 2-(2-hydroxyphenyl)benzotriazole, 2-acryloxyethoxyhydroxylbenzophenone, phenol-2-(5-chloro-2H-benozotriazol-2-yl)-6-(1,1-)dimethyl-4-methyl, 4-benzoyl-3-hydroxyphenyl-2-methacrylate, 2-[4-(2h-1,2,3-benzotriazol2-yl)-3-hydroxyphenoxy]ethyl-2-methacrylate and any combinations thereof.

According to another aspect of some embodiments of the present invention, there is provided a composition which includes a polymer or co-polymer and a curcuminoid compound incorporated in or on the polymer or co-polymer, the polymer or co-polymer being derived from a pre-polymerization mixture of monomers which includes at least 50 weight percents acrylate monomers.

In some embodiments of the composition having the curcuminoid compound incorporated therein or thereon, the acrylate monomer is selected from the group consisting of an acrylate, a methacrylate, an aryl acrylate and an aryl methacrylate.

In some embodiments of the composition having the curcuminoid compound incorporated therein or thereon as a natural UV-blocker, the composition is a hydrophobic co-polymeric composition being derived from a pre-polymerization mixture of monomers includes:

a first aromatic acrylate monomer, characterized as forming a first homopolymer having a refractive index that ranges from 1.50 to 1.53;

a second aromatic acrylate monomer, characterized as forming a second homopolymer having a Tg lower by a range of 2° C. to 30° C. than a Tg of the first homopolymer;

a third monomer, characterized as forming a third homopolymer having a Tg lower than 35° C.;

a fourth monomer, characterized as forming a fourth homopolymer which is capable of absorbing water to at least 20% of the total weight of the fourth homopolymer; and a fifth monomer, being a crosslinking monomer,
wherein:

a concentration of the first aromatic acrylate monomer ranges from 50% to 60% of the total weight of the composition;

a concentration of the second aromatic acrylate monomer ranges from 15% to 20% of the total weight of the composition;

a concentration of the third monomer ranges from 10% to 15% of the total weight of the composition;

a concentration of the fourth monomer ranges from 5% to 10% of the total weight of the composition; and a concentration of the fifth monomer ranges from 2% to 5% of the total weight of the composition, as described herein.

According to another aspect of some embodiments of the present invention, there is provided a co-polymeric composition which includes a polymeric backbone composed of a plurality of backbone units covalently linked to one another and a curcuminoid compound incorporated in or on the composition, the backbone units being derived from a pre-polymerization mixture of monomers which includes:

a first aromatic acrylate monomer, characterized as forming a first homopolymer having a refractive index that ranges from 1.50 to 1.53; a second aromatic acrylate monomer, characterized as forming a second homopolymer having a Tg lower by a range of 2° C. to 30° C. than a Tg of the first homopolymer; a third monomer, characterized as forming a third homopolymer having a Tg lower than 35° C.; a fourth monomer, characterized as forming a fourth homopolymer which is capable of absorbing water to at least 20% of the total weight of the fourth homopolymer; and a fifth monomer, being a crosslinking monomer, wherein:

a concentration of the first aromatic acrylate monomer ranges from 50% to 60% of the total weight of the composition; a concentration of the second aromatic acrylate monomer ranges from 15% to 20% of the total weight of the composition; a concentration of the third monomer ranges from 10% to 15% of the total weight of the composition; a concentration of the fourth monomer ranges from 5% to 10% of the total weight of the composition; and a concentration of the fifth monomer ranges from 2% to 5% of the total weight of the composition, as described herein, the composition being formulated for ophthalmic application.

In some embodiments of any of the compositions presented herein, the mixture further includes a curing agent.

In some embodiments of any of the compositions presented herein, the curing agent is selected from the group consisting of a peroxy catalyst, an oxide catalyst, tert-butyl peroxy-2-ethylhexanoate, 2,4,6-trimethylbenzoyldiphenylphosphine oxide and any combinations thereof.

In some embodiments, any of the compositions presented herein further includes an additive selected from the group consisting of a dye, a yellow dye/blue light blocker, a coating material, a heparin coating agent, a photochromic coating agent, a light-stabilizer, a pharmaceutical agent, a cell receptor functional group, a protein group, a viscosity agent, a diluent and any combination thereof.

In some embodiments, the compositions presented herein are having a visible light transmission of at least 97% of incident visible light.

In some embodiments, the compositions presented herein are having a refractive index of at least 1.53.

In some embodiments, the compositions presented herein are having loop pull force mechanical strength of at least 60 grams.

In some embodiments, the compositions presented herein are characterized by a glass transition temperature not higher than 5° C.

In some embodiments, the compositions presented herein are characterized by Shore A hardness that ranges from 77 to 80.

In some embodiments, the compositions presented herein are having an unfolding time of less than 6 seconds.

In some embodiments, the compositions presented herein are characterized by having essentially no internal reflections.

In some embodiments, the compositions presented herein are characterized by having essentially no vacuoles and/or perceivable glistening.

In some embodiments, the compositions presented herein are having a leachable content of less than 0.6%.

In some embodiments, the compositions presented herein are essentially tack free.

In some embodiments of the compositions presented herein which include a curcuminoid compound, the concentration of the curcuminoid compound ranges from 0.0002 weight percentage to 1 weight percentage of the total weight of the composition.

In some embodiments of the compositions presented herein, the concentration of the curcuminoid compound decreases by less than 0.0001 weight percentage when the composition is subjected to a solvent extraction.

In some embodiments, the curcuminoid compound containing compositions presented herein are substantially transparent to light at a wavelength ranging from about 400 to about 800 nm.

In some embodiments, the curcuminoid compound containing compositions presented herein are substantially opaque to light at a wavelength ranging from about 190 to about 440.

In some embodiments of the compositions presented herein which include a curcuminoid compound, the curcuminoid compound is selected from the group consisting of curcumin, bisdemethoxycurcumin, monodemethoxycurcumin and tetrahydroxycurcumin.

In some embodiments, any of the compositions presented herein is identified for use in the manufacturing of an ophthalmic or ocular device.

In some embodiments, the ophthalmic or ocular device is selected from the group consisting of an intraocular lens (IOL), a contact lens, an implantable ocular device, a keratoprosthesis, a phakic lens, an aphakic lens, a corneal ring, a capsular bag extension ring, a corneal inlay and a corneal onlay.

According to another aspect of some embodiments of the present invention, there is provided a process of preparing the compositions as presented herein, which is effected by:

admixing the pre-polymerization mixture of monomers and a free radical polymerization initiator;

heating the pre-polymerization mixture to 40° C. while stirring until a viscosity reach 120 cps at 25° C.;

degassing the pre-polymerization mixture so as remove volatile residues;

admixing an additional amount of the initiator into the pre-polymerization mixture so as to obtain a reaction mixture;

admixing a curing agent into the reaction mixture;

casting the reaction mixture into a mold;

exposing the reaction mixture to curing conditions, to thereby obtain the composition.

In some embodiments, the process presented herein further includes, prior to the casting, filtering the reaction mixture.

In some embodiments, the process presented herein further includes, subsequent to the exposing the reaction mixture to the curing conditions, subjecting the composition to a multiple extraction.

In some embodiments, the process presented herein further includes, subsequent to the exposing the reaction mixture to the curing conditions, exposing the composition to a treatment selected from the group consisting of a plasma treatment, a surface fluorination, a bulk fluorination, a hydrophilic coating, an electron beam irradiation, a high energy UV irradiation, a energy intensive irradiation, a internal wetting agent and any combination thereof.

In some embodiments of the process presented herein, the multiple extraction includes releasing the composition from the mold; and sequentially immersing the composition in a series of solvent baths to thereby extract unreacted contaminants.

In some embodiments, the process presented herein further includes, subsequent to the exposing the reaction mixture to the curing conditions, polishing and/or machining the composition so as to obtain a final form.

According to another aspect of some embodiments of the present invention, there is provided an ophthalmic or ocular device which is formed substantially from the compositions presented herein.

In some embodiments, the device is selected from the group consisting of an intraocular lens (IOL), a contact lens, an implantable ocular device, a keratoprosthesis, a phakic lens, an aphakic lens, a corneal ring, a capsular bag extension ring, a corneal inlay and a corneal onlay.

In some embodiments, the device is identified for use in the treatment of an optical distortion, retinopathy, a retinal detachment, an occlusion, proliferative retinopathy; proliferative vitreoretinopathy, diabetic retinopathy, a degenerative disease and an age-related macular degeneration.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings.

DESCRIPTION OF SPECIFIC EMBODIMENTS OF THE INVENTION

Figure 1:
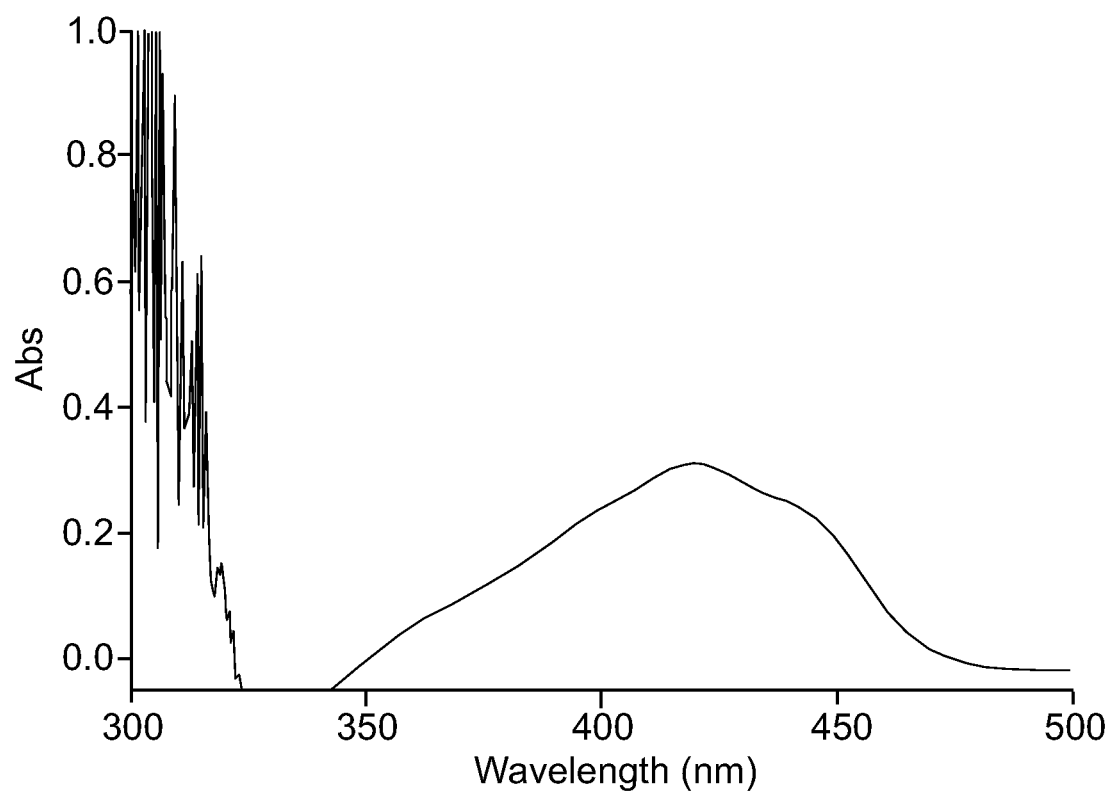
FIG. 1 presents the UV-Vis absorption spectra of a sample of curcumin after purification on a preparative silica gel column at 25° C., using a mixture of chloroform and ethyl acetate (9:1 ratio)

The present invention, in some embodiments thereof, relates to polymeric and co-polymeric materials, and more particularly, but not exclusively, to polymeric and co-polymeric materials useful for preparing ocular devices such as intraocular, ophthalmic implants and contact lenses.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Shape and composition of optical devices determine their interaction with light. While the shape of an optical device such as a lens mainly controls refractive and diffractive aspects, the composition mainly controls absorptive, refractive and reflective aspects. Light transmissive polymeric materials have been used for decades to construct optical devices as corrective measures for refractive errors and other conditions of failing eye sight and vision. Such materials have been found suitable for lenses due to the ease of forming various complex and precise shapes therefrom, using casting, molding, machining, polishing and various combinations of these industrial techniques, and due to the relative chemical stability of such polymeric compositions under various conditions.

Yet, presently known polymeric compositions used in the manufacturing of ophthalmic and ocular devices, and particularly implantable devices, suffer from a variety of shortcomings, including, for example, bio-incompatibility, leachable contaminants, degradation in physiological conditions, UV vulnerability, incompatible refractive index, internal reflections, tackiness, glistening, vacuoles, high cost of materials and manufacturing complexities.

As discussed hereinabove, presently known UV-blocking and light stabilizing additives and synthetic chromophores, used in polymeric compositions for ophthalmic and ocular devices, suffer from one or more drawbacks, including biocompatibility, physical, mechanical and chemical stability, and manufacturing factors (e.g., cost and complex syntheses).

The present inventors have sought a comprehensive solution to a group of problems associated with ophthalmic and ocular devices made from polymeric and/or co-polymeric compositions, including biocompatible and UV-light stabilized materials. The present inventors further contemplated the unique UV-stabilizing effect of curcuminoid compounds for devising a UV-stabilized polymeric-based multifocal ophthalmic device.

In general, ophthalmic and ocular devices differ from spectacles (eye-glasses) and other optical devices, by being designed to be in direct contact with the living tissue of the eye or its immediate surroundings. The devices which come in such direct contact are required to be biocompatible, as discussed herein, as well as to have certain physical properties with respect to their mechanical reshapability and reformability, flexibility, water-absorption capacity, and the likes. Implantable devices differ from non-implantable devices mainly by their mode of use and administration as well as their term of use, namely the devices that require a surgical procedure in order to be put in place are typically referred to as implantable. Implantable ophthalmic and ocular devices are expected to last longer and thus the requirements for their stability and compatibility in all aspects are much higher.

The term "bio-compatible", as used in reference to polymeric and co-polymeric compositions as presented herein, refers to the non-toxic and benign effect that the composition has on a living tissue (e.g., an eye or a portion or a component thereof) when in contact therewith.

The term "chemo-compatible", as used in reference to polymeric and co-polymeric compositions as presented herein, refers to the long-term non-leachability of unreacted components and diluents, non-degradability and overall long-term chemical stability of the composition when in contact with a living tissue in the eye and exposed to ambient light.

The term "physico-compatible", as used in reference to polymeric and co-polymeric compositions as presented herein, refers to the optical properties of the compositions in terms of refractive index, internal reflections, light transmission and/or absorbance, and other properties relating to light-matter interaction.

As used herein, the phrase "ophthalmic and ocular device", refers to devices that reside in or on the eye. These devices can provide optical correction, lens replacement, wound care, drug delivery, diagnostic functionality, cosmetic enhancement or effect or a combination of these properties. The phrase "ophthalmic and ocular device", as used herein, encompasses, but is not limited to, soft contact lenses, hard contact lenses, intraocular lenses (IOLs), implantable lenses, keratoprostheses, phakic and aphakic lenses, corneal overlay and inlay lenses, ocular inserts, corneal rings, capsular bag extension rings, and optical inserts.

The ophthalmic and ocular device of the present embodiments can be fabricated in any technique known in the art. A formed (molded) and cured polymeric or co-polymeric composition can be unprocessed or partially post-processed by machining, in which case polishing and mass subtraction determines the final shape and finish of the device, as known in the art.

Improved Polymeric or Co polymeric Compositions for Ophthalmic Applications:

According to an aspect of some embodiments of the present invention there are provided polymeric or co-polymeric compositions which are suitable for use in ophthalmic applications.

In some embodiments of the present invention, the polymeric or co-polymeric compositions presented herein are derived from a pre-polymerization mixture of monomers. In polymeric compositions, the monomers in the mixture are the same whereby in co-polymeric compositions several different classes of monomers are used. As in any polymer, the polymeric or co-polymeric composition is based on plurality of polymeric backbones, each of which consists of a plurality of backbone units which are covalently attached to one another, and each of the backbone units comprises a plurality of building-blocks or polymerized monomeric units. Hence, the composition, which is the outcome of polymerizing a pre-polymerization mixture of monomers, can be characterized and defined at the chemical and physical property level, in terms of the pre-polymeric mixture, namely its constituents prior to polymerization.

The monomers which are put into the pre-polymerization mixture are still unreacted (not yet polymerized) and are regarded as the starting materials for the compositions presented herein. In the case of a co-polymeric composition, each of the monomers, identified and classified into classes, can be characterized by chemical and physical properties exhibited by the corresponding homopolymer which is derived from each of the individual monomer in the class. Hence, co-polymeric compositions as presented herein can be characterized by the monomer class which it is derived from, as well as the relative amount-ratios between each monomer class in the pre-polymerization mixture.

As used herein, the term "monomer" is used to describe a constituent of the pre-polymerization mixture which affords, upon polymerization, the polymeric or co-polymeric compositions presented herein. It is noted herein that while some of the constituents of the pre-polymerization mixture participate in the polymerization process as reactants which form covalent bonds with other constituents in the mixture during the polymerization process, some may not react with other constituents in a covalent-bond-forming reaction, but become embedded or incorporated within the matrix of the polymeric or co-polymeric composition, as will be discussed hereinbelow.

According to some embodiments of the present invention, a pre-polymerization mixture as described herein may include any of the monomers as described herein, as a starting material, in its monomeric form, or, alternatively, as a polymeric building block, which typically has a relatively low average molecular weight of about less than 2000 Daltons (as measured via gel permeation chromatography refractive index detection). According to other embodiments of the present invention, the starting material can include dimmers of a monomer (two monomeric units or building blocks) and in some cases be a short oligomer of building blocks, including oligomers made from more than one type of monomeric unit. Short oligomers are commonly referred to in the art as "blocks".

It is noted that a polymeric or co-polymeric composition of the present embodiments is compatible for use in the eyes and is optically clear and suitable for use as material of construction of ophthalmic and ocular device. By optically clear it is meant that the composition is essentially transparent to visible light, as described and defined herein.

The term "transparent", used herein in the optical sense, describes the physical property of a substance to allow light to pass (transmit) therethrough. The term "transparent" is used herein as the opposite to the term "opaque", and it is not used to refer to translucency or translucidity (partial transparency). Hence, in the context of the present embodiments, a transparent substance is clear, and exhibits pellucidity or diaphaneity. The term transparent does not necessarily refer to other manifestations of light-matter interactions such as diffraction, refraction or dispersion. Accordingly, the term "opaque", used herein in the optical sense, describes the physical property of a substance to block (absorb) light from passing (transmitting) therethrough.

The properties of transparency and opacity may be wavelength dependent, meaning that the same substance may be transparent with respect to light of a certain range of wavelengths, while at the same time be opaque with respect to light of another range of wavelengths, hence acting like a wavelength-selective filter of light. In the context of the present embodiments, a substantially transparent composition allows at least 98% of the light intensity of a given range of wavelength to pass therethrough (a maximal loss of 2% of the light's intensity), while a substantially opaque composition reflects, scatters or absorbs more than 98% of the incoming light of a given range of wavelength, allowing less than 2% of the light to pass therethrough. Alternatively, transparency is defined as transmission of 95% of the light intensity of a given range of wavelength.

Visible light, as defined by the visibility of a typical human eye, is characterized by a wavelength ranging from 390 nm to 750 nm. According to some embodiments of the present invention, the composition for making the ophthalmic devices presented herein is characterized by being substantially transmissive (transparent) to visible light.

Hydrophobic Co polymeric Compositions for Ophthalmic Applications:

According to an aspect of some embodiments of the present invention, there are provided co-polymeric compositions which are suitable for use in ophthalmic applications.

The co-polymeric compositions presented herein are based on five matrix-forming constituents as well as other ingredients such as catalyst, UV-stabilizer/UV-blocker and high energy visible blue light stabilizer. The compositions may further comprise colorant/dye additives, leachable agents (drugs) and the likes.

The co-polymeric composition presented herein typically and advantageously exhibits relatively high refractive indexes when in its final form and fully hydrated. The refractive index of the final and fully hydrated co-polymeric composition presented herein, is typically greater than about 1.5, more typically greater than about 1.51, still more typically greater than about 1.52 and even possibly greater than 1.53 or even 1.54, wherein the refractive index of the fully hydrated composition is measured at 25° C. in accordance with ASTM D 542-00 (2006).

Hence, according to some embodiments of the present invention, there is provided a co-polymeric composition, being formulated for ophthalmic application, the composition being derived from a mixture of monomers that include:

a first aromatic acrylate (aryl acrylate) monomer characterized as forming, upon polymerization thereof, a first homopolymer which exhibits a refractive index that ranges from 1.50 to 1.53;

a second aromatic acrylate (aryl acrylate) monomer characterized as forming, upon polymerization thereof, a second homopolymer, which exhibits a Tg (glass transition temperature) lower than the Tg of the homopolymer derived from the first monomer by a range of 2 to 30 degrees centigrade;

a third monomer characterized as forming, upon polymerization thereof, a third homopolymer, which exhibit a Tg lower than 35° C. or lower than 37° C.;

a fourth monomer characterized as forming, upon polymerization thereof, a fourth homopolymer, which exhibit a capacity to absorb water to at least 20% of its dry weight; and a fifth monomer serving a crosslinking agent, wherein:

a concentration of the first aromatic acrylate monomer ranges from 50% to 60% of the total weight of the composition;

a concentration of the second aromatic acrylate monomer ranges from 15% to 20% of the total weight of the composition;

a concentration of the third monomer ranges from 10% to 15% of the total weight of the composition;

a concentration of the fourth monomer ranges from 5% to 10% of the total weight of the composition; and a concentration of the fifth monomer ranges from 2% to 5% of the total weight of the composition.

It is noted that the co-polymeric compositions presented herein, which are formed from a number of monomer classes, referred to herein as a first, second, third, fourth and fifth monomers, can include a variety of different monomers of each class, namely one or any number of monomers mentioned within the class of monomers corresponding to the first, second, third, fourth or fifth monomer.

Unless otherwise stated, the percentages (e.g., weight percentages) of the constituents of the co-polymeric composition presented herein are denoted as weight percentages of the starting material with respect to the total weight of the pre-polymerizable mixture.

According to some embodiments of the present invention, the co-polymeric composition presented herein contains less than 75% in total of aryl acrylate monomers.

The major component of the co-polymeric composition is nevertheless based on aryl acrylate, as opposed to mixtures of aryl methacrylate and aryl acrylate which are known in the related art, which is less suitable for producing an ophthalmic and ocular device as presented herein.

One disadvantage of using aryl acrylate and aryl methacrylate/acrylate in more than 80% concentration is the occurrence of internal reflections and glare which may appear in the device made from such co-polymeric composition. This disadvantage is mitigated by strictly controlling the content of any aryl-containing monomer.

In general, every monomer adds from its associated property to co-polymeric composition, and when all property adds up in a prerequisite proportion, they form a co-polymeric composition suiting the desired application.

The fifth monomer (class) is a crosslinking agent, as defined hereinbelow, interchangeably referred to herein as a crosslinker, which is characterized according to its capacity to alter the strength, rigidity and consistency of the co-polymeric composition presented herein. Thus, the cross-linking monomer (the fifth monomer) is a component having an effect on controlling flexibility of the obtained material for a soft embodiment of composition presented herein, giving the desired mechanical strength, improving capability of deformation recovery, and increasing co-polymerizable property with components for polymerization. Co-polymeric compositions which are not cross-linked may deteriorate rapidly as polymer chains are loosely held and increasing the possibility of getting extracted out under soxhlation extraction (gel content), resulting into loss of strength, loss of shape recovery and higher occurrence of vacuoles. The crosslinker is also the constituent that leads to an increase in the molecular weight of the composition (size of an average contiguous chain) by tethering chains to one-another. The molecular weight of the composition has a direct effect on the glistening, mechanical properties, refractive index and many other mechanical and optical properties of the composition and subsequently a device made therefrom.

The first monomer (class) is an aromatic-containing (or aryl-containing) acrylate type monomer (hence, a first aromatic monomer) which is characterized as forming, upon polymerization thereof, a first homopolymer having a refractive index between 1.50-1.53 (a criterion for selecting the first monomer). As a constituent of the co-polymeric compositions presented herein, the first monomer can include one or more monomer structures, namely different monomers wherein each satisfies at least the aforementioned criterion.

Acrylate monomers constitute a family which is a type of vinyl monomers, or esters which contain a vinyl group, namely two carbon atoms double-bonded to each other, directly attached to the carbonyl carbon of a carboxyl group, as illustrated in Scheme 1 below.

Scheme 1

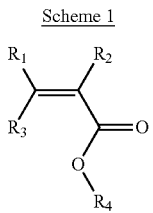

The term "methacrylate" refers to an acrylate monomer having a methyl group at position $R_2$ in Scheme 1 above.

The phrase "aromatic acrylate", as used herein, refers to an acrylate ester having an aromatic substituent attached to the carbonyl, denoted $R_4$ in Scheme 1 above.

Accordingly, the phrase "aromatic methacrylate" refers to a monomer as illustrated in Scheme 1 above, wherein $R_2$ is a methyl group and $R_4$ is an aryl or a heteroaryl group.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

Without being bound by a particular theory, the rational behind using aryl ether acrylate monomers is their relatively flexible result-polymer compared to straight chain aryl alkyl methacrylate which adds to greater deforming ability into lens matrix without significantly compromising on refractive index and hydrophobicity.

Exemplary monomers that are suitable for use as a first monomer according to embodiments of the invention include 2-phenoxyethyl acrylate, 2-phenoxy ethyl methacrylate, 2-benzyloxy ethyl acrylate, 2-benzyloxy ethyl methacrylate and combinations thereof.

Other non-limiting examples of the first aromatic acrylate monomer according to some embodiments of the present invention, include 2-ethylphenoxy methacrylate; 2-ethylphenoxy acrylate; 2-ethylthiophenyl methacrylate; 2-ethylthiophenyl acrylate; 2-ethylaminophenyl methacrylate; 2-ethylaminophenyl acrylate; phenyl methacrylate; phenyl acrylate; benzyl methacrylate; benzyl acrylate; 2-phenylethyl methacrylate; 2-phenylethyl acrylate; 3-phenylpropyl methacrylate; 3-phenylpropyl acrylate; 4-phenylbutyl methacrylate; 4-phenylbutyl acrylate; 4-methylphenyl methacrylate; 4-methylphenyl acrylate; 4-methylbenzyl methacrylate; 4-methylbenzyl acrylate; 2-2-methylphenylethyl methacrylate; 2-2-methylphenylethyl acrylate; 2-3-methylphenylethyl methacrylate; 2-3-methylphenylethyl acrylate; 24-methylphenylethyl methacrylate; 2-4-methylphenylethyl acrylate; 2-(4-propylphenyl)ethyl methacrylate; 2-(4-propylphenyl)ethyl acrylate; 2-(4-(1-methylethyl)phenyl)ethyl methacrylate; 2-(4-(1-methylethyl)phenyl)ethyl acrylate; 2-(4-methoxyphenyl)ethyl methacrylate; 2-(4-methoxyphenyl)ethyl acrylate; 2-(4-cyclohexylphenyl)ethyl methacrylate; 2-(4-cyclohexylphenyl)ethyl acrylate; 2-(2-chlorophenyl)ethyl methacrylate; 2-(2-chlorophenyl)ethyl acrylate; 2-(3-chlorophenyl)ethyl methacrylate; 2-(3-chlorophenyl)ethyl acrylate; 2-(4-chlorophenyl)ethyl methacrylate; 2-(4-chlorophenyl)ethyl acrylate; 2-(4-bromophenyl)ethyl methacrylate; 2-(4-bromophenyl)ethyl acrylate; 2-(3-phenylphenyl)ethyl methacrylate; 2-(3-phenylphenyl)ethyl acrylate; 2-(4-phenylphenyl)ethyl methacrylate; 2-(4-phenylphenyl)ethyl acrylate; 2-(4-benzylphenyl)ethyl methacrylate; and 2-(4-benzylphenyl)ethyl acrylate, and the like.

Additional examples for suitable first monomers include naphthyl acrylates, dicyclopentyloxy acrylates, dicyclopentyl acrylates, nonylphenoxy polyethyleneglycol 200 acrylates, nonylphenoxy polyethyleneglycol 400 acrylates, alkoxylated phenol acrylates, 2-methacryloyloxyethyl 2-hydroxy propyl phthalates, 2-acryloxy ethyl-2-hydroxy ethyl phthalates, 2-hydroxy-3-phenoxy propyl acrylates, neopentyl glycol benzoate acrylates and the likes.

According to some embodiments of the present invention, the concentration of the first monomer ranges from 52% to 59% of the total weight of the composition.

The second monomer (class) is another aromatic acrylate monomer characterized as forming, upon polymerization thereof, a second homopolymer having a Tg lower than the Tg of the first homopolymer, which is derived from the first monomer, by 2 to 30 degrees centigrade (° C.).

Non-crystalline polymeric solids are referred to as amorphous materials (atoms or molecules are not arranged in a lattice that repeats periodically in space). For all amorphous solids, whether glasses, organic polymers, and even metals (although having a lattice), Tg is the critical temperature that separates their glassy and rubbery behaviors. A glass is defined as a material that has no long-range atomic or molecular order and is below the temperature at which a rearrangement of its atoms or molecules can occur. On the other hand, a rubber is a non-crystalline solid whose atoms or molecules can undergo rearrangement. If a material is at a temperature below its Tg, large-scale molecular motion is not possible because the material is essentially frozen. If it is at a temperature above its Tg, molecular motion on the scale of its repeat unit (such as 50-mer in a polymer) takes place, allowing it to be "soft" or "rubbery". It is noted that the term "Tg" is applies herein to non-crystalline solids, which are mostly either "glasses" or "rubbers".

Hence, the phrases "glass transition temperature" or "rubber-glass transition temperature", as used herein in the context of polymers, refers to the temperature at which the Gibbs free energy is such that the activation energy for the cooperative movement of about 50 elements (50-mer) of the polymer is exceeded compared to a reference point, meaning that molecular chains are able to slide past each other when a force is applied. A glass transition temperature of a non-crystalline material, such as a polymer, is the critical temperature at which the material changes its behavior from being "glassy" to being "rubbery", while lowering the temperature across the Tg affords vitrification. "Glassy" in this context means hard and brittle (and therefore relatively easy to break), while "rubbery" means elastic and flexible and can absorb kinetic energy without shuttering.

According to some embodiments of the present invention, the chemical structure of the second monomer can follow the same chemical rational characterizing the first monomer, with the difference that the second monomer is selected according to the Tg characterizing the second homopolymer being lower than the Tg of the first homopolymer by 2-30° C.

The choice of a second aromatic monomer according to embodiments of the invention include, depends on the choice of the first monomer as difference in relative Tg is the criterion for selecting the second monomer. Therefore, there is much overlap in the range of options of the first and the second monomers.

Exemplary monomers that are suitable for use as a second aromatic monomer according to embodiments of the invention include, but are not limited to 2-phenylethyl acrylate, benzyl acrylate, 4-methyl benzyl acrylate, 2,4,6-tribromophenyl acrylate, pentabromophenyl acrylate and any combinations thereof.

According to some embodiments of the present invention, the concentration of the second monomer ranges from 15% to 19% of the total weight of the composition.

It is noted herein that some ophthalmic and ocular devices, and particularly implantable devices, are required to avoid posterior capsular opacification (PCO) after cataract replacement surgery. This adverse effect is related also to the tackiness of the composition. To control tackiness, suitable monomers are selected for the co-polymeric composition, while not compromising the refractive index of the resulting composition. Hence, the co-polymeric composition presented herein exhibits tackiness to some degree so as to avoid PCO, and therefore tackiness should be high enough to reduce PCO, and low enough so as not to hinder handling.

Thus, the first monomer is meant to be restricted to the above-mentioned range, since the first monomer is characterized by a relatively higher Tg which makes the resulting polymer less tacky than the polymer resulting from the second monomer. These formulation restrictions confer relatively low tackiness without compromising the target refractive index. At the same time, the reason for keeping a high Tg monomer (higher than a low Tg monomer), is to confer mechanical strength to the composition, which increases due to higher crystallinity impartment thereto.

It is further noted herein that according to some embodiments of the present invention, a relatively high Tg aryl monomer is used as a major constituent, while the prior art teaches the use of lower Tg aryl monomer as a major part of the composition. For example, U.S. Pat. No. 5,290,892 teaches the use of 2-phenyl ethyl acrylate in higher amount compared to 2-phenyl ethyl methacrylate, while methacrylate compounds have higher Tg compared to corresponding acrylate compound. Together it forms at least 80% of the composition taught in U.S. Pat. No. 5,290,892.

The third monomer (class) is characterized as forming, upon polymerization thereof, a third homopolymer having a Tg lower than 37° C. The third monomer is the component which has a notable effect on the flexibility of the obtained composition, conferring softness to the device, and improving its capability to recover from deformation. The capacity to recover quickly from deformation (reformability) is required by an ophthalmic device when applied to the eye after folding and while following the shape shifts of the eye.

Exemplary monomers that are suitable for use as a third monomer according to embodiments of the invention include, but are not limited to, cellosolve methacrylate, methoxy ethyl acrylate, polyethylene glycol monomethacrylate, 1-dihydroxyperfluorobutyl methacrylate, 2,5-dibromopropyl methacrylate, hexyl methacrylate, glycerol monomethacrylate, trifluoroethyl methacrylate, butyl methacrylate, n-ocyl/isooctyl methacrylate, n-decyl/isodecyl methacrylate, ethyl methacrylate, ethylene triglycol methacrylate, butyl diglycol methacrylate, methoxy polyethylene glycol 350 methhacrylate, methoxy polyethylene glycol 500 methhacrylate, methoxy polyethylene glycol 1000 methhacrylate, methoxy polyethylene glycol 2000 methhacrylate. methoxy polyethylene glycol 5000 methhacrylate, polypropylene glycon methacrylate, ethoxytriglycol methacrylate, 2-ethoxyethoxy ethyl methacrylate, methoxy triethyleglycol methacrylate, phenoxy polyethylene glycol monomethacrylate and any combinations thereof.

According to some embodiments of the present invention, the concentration of the third monomer ranges from 11% to 15% of the total weight of the composition.

It is noted herein that use of aryl ether acrylate and aryl alkyl acrylate, such as 2-phenoxy ethyl acrylate and 2-phenyl ethyl acrylate, gives superior results over the use of methacrylate and acrylate of same pendant group as described in the art.

Methacrylate groups are known to increase the rigidity of the resultant polymer, since methacrylate compounds exhibit side chain crystallization thereby increasing rigidity. According to some embodiments of the present invention, it is suggested herein to introduce high Tg aryl ether acrylate monomer which also imparts flexibility to the co-polymeric composition, enabling 20D IOL delivery even through a sub 2 mm incision in a wound assisted surgical technique. An additional advantage of using aryl ether acrylate is its relatively less tacky nature compared to aryl alkyl methacrylate.

By using lesser amount of aryl acrylate monomer, polymer of relatively low refractive index is prepared to avoid glare/internal reflection problem at the same time, refractive index is maintained to a level that it would enable the lens to go through sub 2 mm incision.

For increasing strength and reformability, monomers like methoxy ethyl methacrylate are used. Its Tg is lower than 37° C. and it forms relatively hydrophobic polymer than conventional 2-ethoxy ethyl methacrylate. In general, in the pendant ether group, odd number of methylene ($CH_2$) gives optimal results. Examples include methoxy ethyl acrylate, propoxy ethyl acrylate, pentoxy ethyl acrylate and the likes.

The fourth monomer (class) is a hydrophilic monomer which is characterized as forming, upon polymerization thereof, a fourth homopolymer exhibiting a capacity to absorb water to at least 20% of its dry weight.

Water content of the homopolymer made from hydrophilic monomer should absorb enough so as to conform to the requirement of ophthalmic devices such as contact lenses and IOLs. After extraction of the leachables from the formulation, a process that is discussed hereinbelow, vacuoles may form in the product. Hence, all hydrophobic polymeric compositions exhibit vacuoles and some water absorption. When ophthalmic device comes in a contact with water or another aqueous medium, these media would tend to concentrate at the vacuoles.

Prime purpose of using a hydrophilic monomer is to uniformly disperse the water in the matrix. After putting the ophthalmic device in physiological medium like normal saline or highly pure water, these vacuoles give rise to white spots. To overcome this problem, hydrophilic monomer would disperse water uniformly rather than allowing water to concentrate in voids and vacuoles. This uniform dispersion gives rise to clear and spotless lenses. It also helps to increase the strength of the matrix and to control its tackiness.

Some commonly available hydrophilic monomer absorbs more than 20% of the total weight of their corresponding homopolymer. If the required water content in the composition should be kept bellow 20%, other monomers can be selected so as to counter-effect the absorption of water.

The forth monomer is also effective to reduce tackiness of the co-polymeric composition presented here, as well as to improve its mechanical properties, as well as to uniformly disperse water molecules throughout the matrix at a wide temperature change.

As used herein, the phrase "hydrophilic monomer" refers to compounds which produce hydrogel-forming homopolymers, namely homopolymers which become associated with substantial amounts of water (for example, at least 20% based on the weight of the dry homopolymer), and which physically swell as a result of such association.

Exemplary fourth monomers include, without limitation, alkoxy alkyl(meth)acrylate; N-vinyl pyrrolidone; hydroxyalkyl acrylates and hydroxyalkyl methacrylates, such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2,3-dihydroxypropyl acrylate, 2,3-dihydroxypropyl methacrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and mixtures thereof.

Additional exemplary monomers that are suitable for use as a fourth monomer according to embodiments of the invention include, but are not limited to, hydroxyethyl methacrylate, glycerol monomethacrylate, ethylene triglycol methacrylate, butyl diglycol methacrylate, methoxy polyethylene glycol 350 methhacrylate, methoxy polyethylene glycol 500 methhacrylate, methoxy polyethylene glycol 1000 methhacrylate, methoxy polyethylene glycol 2000 methhacrylate, methoxy polyethylene glycol 5000 methhacrylate, polypropylene glycon methacrylate, ethoxytriglycol methacrylate, methoxy triethyleglycol methacrylate, phenoxy polyethylene glycol monomethacrylate and any combinations thereof.

According to some embodiments of the present invention, the concentration of the fourth monomer ranges from 7% to 9% of the total weight of the composition.

As used herein, the phrase "cross-linking monomer" refers to a substance that promotes or regulates intermolecular covalent, ionic, hydrophobic or other form of bonding between polymer chains, linking them together to create a network of chains which result in a more rigid structure. Crosslinking monomers, according to some embodiments of the present invention, contain at least two reactive groups that are reactive towards a variety of groups, including double bonds, sulfhydryls and amines, and create chemical bonds between two or more polymer molecules. Crosslinking monomers include homo-bifunctional crosslinking monomers that have two identical reactive end groups, and hetero-bifunctional crosslinking monomers which have two different reactive end groups. These two classes of crosslinking monomers differ primarily in the chemical reaction which is used to effect the crosslinking step, wherein homo-bifunctional crosslinking monomers will require a one step reaction, and hetero-bifunctional crosslinking monomers will require two steps to effect the same. While homo-bifunctional crosslinking monomers have the tendency to result in self-conjugation, polymerization, and intracellular cross-linking, hetero-bifunctional agents allow more controlled two step reactions, which minimize undesirable intramolecular cross reaction and polymerization. Crosslinking monomers are further characterized by different spacer arm lengths. A crosslinking monomer with a longer spacer arm may be used where two target groups are further apart and when more flexibility is desired.

Exemplary crosslinking monomers include, without limitation, butanediol di(meth)acrylate, ethylene glycol di(meth)acrylate, diethylene glycol di(meth)acrylate, triethylene glycol di(meth)acrylate, propylene glycol di(meth)acrylate, dipropylene glycol di(meth)acrylate, diallyl fumarate, allyl (meth)acrylate, vinyl(meth)acrylate, trimethylolpropane tri(meth)acrylate, methacryloyloxyethyl(meth)acrylate, divinylbenzene, diallyl phthalate, diallyl adipate, triallyl diisocyanate, α-methylene-N-vinylpyrrolidone, 4-vinylbenzyl(meth)acrylate, 3-vinylbenzyl(meth)acrylate, 2,2-bis((meth)acryloyloxyphenyl)hexafluoropropane, 2,2-bis((meth)acryloyloxyphenyl)propane, 1,4-bis(2-(meth)acryloyloxyhexafluoroisopropyl)benzene, 1,3-bis(2-(meth)acryloyloxyhexafluoroisopropyl)benzene, 1,2-bis(2-(meth)acryloyloxyhexafluoroisopropyl)benzene, 1,4-bis(2-(meth)acryloyloxyisopropyl)benzene, 1,3-bis(2-(meth)acryloyloxyisopropyl)benzene, 1,2-bis(2-(meth)acryloyloxyisopropyl)benzene, and the like. These crosslinking monomers can be used solely or in a combination use of two or more thereof. Among those, ethylene glycol dimethacrylate and butanediol diacrylate are widely use effect controllable flexibility, desired mechanical strength, improved capability of deformation recovery, and increased co-polymerizable property.

Additional exemplary monomers that are suitable for use as a fifth monomer according to embodiments of the invention include, but are not limited to ethylene glycol dimethacrylate, 1,4-butane diol diacrylate, glycerol dimethacrylate, allyl methacrylate, 1,6 hexane diol diacrylate, 1,4-butanediol dimethacrylate, 1,6-hexane diol dimethacrylate and any combinations thereof.

According to some embodiments of the present invention, the concentration of the fifth monomer ranges from 2% to 3.5% of the total weight of the composition.

The amount of the fifth monomer (crosslinker) depends on selection of the prior monomers. It is added to have an optimal shape recovery, to lessen the extractables and reduce glistening. An excess amount may increase glistening of composition after introduction into physiological medium. Lesser amount may result into loss of strength, higher extractables (more vacuoles) and slower shape recovery.

In addition, the co-polymeric compositions presented herein can include a variety of additional or alternative ingredients, feature additives and the likes. Examples include, without limitation, UV blockers, dyes, light-stabilizers, coating materials, pharmaceuticals (therapeutic agents), cell receptor functional groups, protein groups, viscosity agents (e.g., thickeners or thinners), diluents, combinations thereof or the like.

As discussed hereinabove, each and every constituent in the co-polymeric compositions presented herein, as well as their relative proportion in the making thereof, contribute to the wide range of requirements and necessary characteristics of these compositions.

For example, according to some embodiments of the present invention, the compositions presented herein exhibit visible light transmission of at least 97% of incident visible light, as determined according to ASTM D 1003 standard and/or ISO 11979-2:2000 standard.

In addition, the compositions presented herein exhibit a refractive index of at least 1.53, as determined according to the ASTM D 542-00 (2006) standard.

In addition, or alternatively, according to some embodiments of the present invention, the co-polymeric compositions presented herein exhibit a loop pull force mechanical strength of at least 60 grams, at least 50 grams or at least 40 grams, as determined according to the ISO 11979-3:2006 standard.

In addition, or alternatively, the co-polymeric compositions presented herein are further characterized by a glass transition temperature not higher than 5° C., not higher than 10° C. or not higher than 15° C., as determined according to the ASTM D3418-03:2000 standard.

In addition, or alternatively, Shore A hardness exhibited by the co-polymeric compositions according to some embodiments of the present invention, ranges from 77 to 80, as determined according to the ASTM D2240:2000 standard.

In addition, or alternatively, according to some embodiments of the present invention, the co-polymeric compositions presented herein exhibit an unfolding time of less than 6 seconds for full recovery of original shape injected through a sub 2 mm cartridge at room temperature. Such requirement is important when a device made of the composition is placed in position by inserting it under leaving tissue with a narrow gauge cartridge (sub 2 mm).

The co-polymeric composition according to some embodiments of the present invention, is characterized by having essentially no internal reflections, and further have essentially no vacuoles and/or perceivable glistening as determined by visual inspection at a magnification of 50×.

One of the requirements of an ophthalmic or ocular device, involving leachable content, is clearly met by the co-polymeric compositions presented herein, which have a leachable content of less than 0.6%, as determined according to the ISO 11979-5:2006 and/or the ISO 11979-5:2006 standards.

According to some embodiments of the present invention, the co-polymeric compositions presented herein are essentially tack-free, as determined according to the ASTM D 3654 standard.

The co-polymeric compositions as described herein can also be referred to as hydrophobic co-polymeric compositions.

An ophthalmic or ocular device made from the co-polymeric compositions presented herein can also be referred to as a hydrophobic diffractive ophthalmic device and can be, for example, a hydrophobic diffractive IOL.

According to some embodiments of the present invention, the co-polymeric compositions presented herein further includes a radiation-resistant compound, which is typically referred to as a UV-blocker agent or additive, UV-light stabilizer and/or UV-absorbent agent. The terms "UV-blocker" and "UV-stabilizer", and grammatical diversions and inflections thereof, are used herein interchangeably, since stabilizing a polymeric composition against the degradation caused by UV-light stems also from the capacity to block UV-light by the composition.

The role of protection from UV damages, both to the eye (protect light sensitive retina) and the co-polymeric composition itself, can be taken by one type of UV-blocker or a combination of several different compounds, some embedded and some co-polymerized with the composition. The UV-blocker can thus be a polymerizable constituent, which presents advantages in terms of leachability of the agent, and it can be an embedded constituent, namely incorporated consistently in the matrix of the polymeric composition so as not to leach out.

It is noted herein that UV-protection is particularly desirable for ophthalmic or ocular devices, which may be located within the eye for extended periods of time (e.g., greater than 6 months, a year, several years or more) as opposed to, for example, disposable contact lenses. As such, it is highly desirable for these types of devices to exhibit longer term resistance to degradation caused by radiation exposure.

An ultraviolet absorbing material (UV-blocker additive or agent) can be any natural or synthetic compound which absorbs ultraviolet light, i.e., light having a wavelength shorter than about 400 nm, but does not absorb any substantial amount of visible light. A natural UV-blocker can be a curcuminoid compound, as defined and discussed herein. The ultraviolet absorbing compound is incorporated into the monomer mixture and is embedded or entrapped in the polymer matrix when the monomer mixture is polymerized. According to some embodiments of the present invention, the UV-blocker provide a transmission cut-off above a wavelength of 385 and typically provide cut-off in the short wavelength visible (410-430 nm) region of the electromagnetic spectrum. Such chromophores can then provide desired protection to the human eye and/or the device material from UV radiation (<400 nm). Suitable UV-blockers can also be referred to as UV/short wavelength visible light absorbers, dye or chromophores.

Unless otherwise specified, "cut-off" means the wavelength at which light transmission does not exceed 1%. "1% cut-off" means the wavelength at which light transmission does not exceed 1%. "10% cut-off" means the wavelength at which light transmission does not exceed 10%.

Typical ultraviolet absorbing compounds, based on synthetic chromophores, include substituted benzophenones, such as 2-hydroxybenzophenone, and 2-(2-hydroxyphenyl) benzotriazoles. According to some embodiments of the present invention, the ultraviolet absorbing compound may be co-polymerizable with the monomers and is thereby firmly embedded in the polymer matrix. In this way possible leaching of the ultraviolet absorbing compound out of the lens and into the interior of the eye is minimized. Suitable co-polymerizable ultraviolet absorbing compounds include substituted 2-hydroxybenzophenones as disclosed in, for example, U.S. Pat. No. 4,304,895 (incorporated by reference as fully set forth herein) and 2-hydroxy-5-acryloxyphenyl-2H-benzotriazoles disclosed in U.S. Pat. No. 4,528,311 (incorporated by reference as fully set forth herein). Alternatively, the ultraviolet absorbing compound is 2-(3'-methallyl-2'-hydroxy-5' methyl phenyl)benzotriazole.

Other synthetic ultraviolet absorbing compounds include phenol-2-(5-chloro-2H-benozotriazol-2-yl)-6-(1,1-)dimethyl-4-methyl (Tinuvin® 326), 4-benzoyl-3-hydroxyphenyl-2-methacrylate, 2-[4-(2h-1,2,3-benzotriazol2-yl)-3-hydroxyphenoxy]ethyl-2-methacrylate and combination thereof.

Optic devices based on co-polymeric compositions may also comprise a polymerizable or embedded yellow dye that attenuates medium- to long-wavelength (430-500 nm) blue light. Such dyes and other useful chromophores are described in U.S. Pat. No. 7,691,918, which is fully incorporated herein for all purposes.

Yellow dye gives a yellowish tint to lens; natural lens tends to get yellow as age of patient progresses. Yellow tinted artificial lens gives the elderly patient the appearance of a natural lens. The yellow dye also provides protection from visible blue light which may lead to age related macular degeneration.

Presently known UV-blocking additives and synthetic chromophores, used in polymeric compositions for ophthalmic and ocular devices, may suffer from one or more drawbacks, including biocompatibility, physical, mechanical and chemical stability, and manufacturing factors (e.g., cost and complex syntheses).

Polymeric or Co-Polymeric Compositions Containing Curcuminoid as a Natural UV-Blocker:

According some embodiments of the present invention, the co-polymeric composition described hereinabove (also referred to herein as a co-polymer or a hydrophobic co-polymeric composition), further includes a natural UV-blocker in the form of a curcuminoid compound incorporated in or on the co-polymeric composition.

In general, curcuminoids can be utilized effectively as UV-blockers in any polymeric or co-polymeric composition useful in ophthalmic application.

Hence, according to another aspect of the present invention, there is provided a polymeric or co-polymeric composition which includes at least one curcuminoid compound, as presented herein, incorporated in or on the composition as a mean of providing UV-light stabilization, wherein the polymeric or co-polymeric composition is derived from a pre-polymerization mixture of monomers.

According to some embodiments of the present invention, polymeric or co-polymeric compositions in which a curcuminoid compound incorporated therein or thereon, is made from a pre-polymerization mixture of monomers which includes at least 50 percents acrylate monomers.

According to some embodiments pertaining to this aspect of the present invention, the acrylate monomer is selected from the group consisting of an acrylate, a methacrylate, an aryl acrylate and an aryl methacrylate.

As demonstrated in the Examples section that follows, one exemplary co-polymer which includes a curcuminoid compound can be formed from one or more monomers such as, but not limited to, 2-phenoxy ethyl methacrylate (POEMA), cyclohexyl acrylate (CHMA) and 1,4-butane diol diacrylate (BDDA). An exemplary composition, according to some embodiments of the present invention, is formed, for example, from a pre-polymerization mixture containing 50-70% 2-phenoxy ethyl methacrylate (POEMA), 20-50% cyclohexyl acrylate (CHMA) and 1-5% 1,4-butane diol diacrylate (BDDA), and 0.001-0.5% curcuminoid compound, each measured by dry weight percentages of the total dry weight of the pre-polymerization mixture. Other constituents may also be included in minor amounts, such as a catalyst (a polymerization initiator agent), cross-linking monomers, colorant/dye additives and the likes.

Alternatively, a co-polymeric composition in or on which a curcuminoid compound is incorporated, can be made from a pre-polymerization mixture which includes the aforementioned five constituents (monomer classes), as described hereinabove. Therefore, some of the above-described embodiments relate to a co-polymeric composition which includes a polymeric backbone composed of a plurality of backbone units covalently linked to one another, which is derived from a pre-polymerization mixture of monomers having a unique formulations as presented herein, and further includes at least one curcuminoid compound, as presented herein, incorporated in or on the composition as a mean to provide UV-light stabilization.

Hence, according to another aspect of the present invention, there is provided a co-polymeric composition formulated for ophthalmic applications (the hydrophobic co-polymeric compositions as described herein), which includes a polymeric backbone composed of a plurality of backbone units covalently linked to one another, which is derived from a pre-polymerization mixture of monomers as described hereinabove, and which further comprises a curcuminoid compound incorporated therein or thereon, as described herein.

Such a composition, which includes a curcuminoid compound in a particular co-polymeric composition, can be prepared essentially as described herein, while the curcuminoid compound is added to the pre-polymerized mixture prior to curing and thereby allowed to be incorporated into the co-polymeric composition.

The term "incorporated", as used herein, refers to the physical state of one substance in a composition containing other substances. In the context of some embodiments of the present invention, an incorporated curcuminoid compound is incorporated within a polymeric or co-polymeric composition as described herein such that the curcuminoid compound is at least partially surrounded by the polymeric or co-polymeric composition and entrapped thereby.

In some embodiments, the incorporated curcuminoid compound is distributed within the polymeric or co-polymeric composition in a uniform and sustainable form, and is enclosed in the surrounding mass.

According to some embodiments of the present invention, the curcuminoid compound incorporated within the polymeric or co-polymeric composition is not covalently attached to one or more constituents of the polymeric or co-polymeric composition. In some embodiments, the curcuminoid compound interacts with the polymeric or co-polymeric composition via physical interactions, such as, for example, entanglement, absorption, adsorption and/or entrapment, and not via chemical interactions such as covalent, ionic, or hydrogen bonds.

Curcuminoids constitute a versatile group of chromophore-containing substances, which can be selected by their light absorption properties to suit a particular application.

In general, curcuminoids are polyphenols characterized by a pronounced yellow color, and most of the naturally occurring curcuminoids, including curcumin itself, have been recognized as generally safe for human consumption and suitable for pharmaceutical purposes.

The term "curcuminoid", as used herein, is used to collectively describe curcumin, as well as derivatized curcumin compounds. Derivatized curcumin compounds have a curcumin backbone structure, and optionally have one or more different chemical groups (substituents) attached at various positions of the curcumin backbone structure. A derivatized curcumin compound may differ from curcumin by chemical and physical characteristics, such as solubility, reactivity, light interaction and the likes, as a result of its substituents.

Curcuminoid compounds according to some embodiments of the present invention, can be collectively represented by General Formula I:

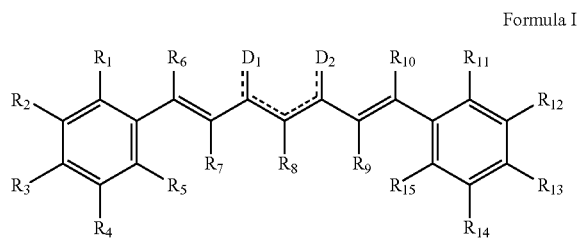

Formula I

According to some embodiments of the present invention, each of $D_1$ and $D_2$ is individually selected from the group consisting of O, N, S or C(aryl), whereas $D_1$ and $D_2$ may be connected directly or via a connecting atom to form a conjugated ring (aryl, heteroaryl etc.); and wherein each of $R_1$-$R_{15}$ is individually selected from the group consisting of alkyl, alkoxy and hydroxy.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

The curcuminoid compound utilized in embodiments of the present invention can be a naturally-occurring curcuminoid or a synthetically prepared curcuminoid, with naturally-occurring curcuminoids being more desirable.

Exemplary curcuminoid compounds that are suitable for use in the context of some embodiments of the present invention include, but are not limited to, curcumin (illustrated in the scheme below), bisdemethoxycurcumin, monodemethoxycurcumin and tetrahydroxycurcumin, which are all natural curcuminoids found in plants such as the curcuma species.

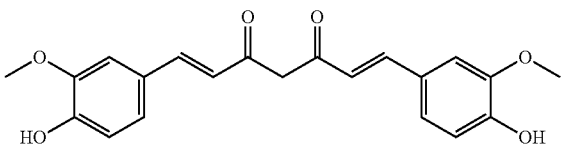

(1E,6E)-1,7-bis(4-hydroxy-3-methoxyphenyl)-6-heptadiene-3,5-dione (Curcumin)

The naturally occurring curcuminoids differ from one another in both the number and position of the methoxy groups, and all exhibit a keto-enol tautomerism in the mid-section of the chromophore chain. These curcuminoids differ in their light absorbing and free radical scavenging properties. All of the naturally-occurring curcuminoids may serve as efficient UV-blockers and/or stabilizers, in the context of embodiments of the present invention. For instance, some natural curcuminoid sources contain tetrahydroxycurcumin (THC), which is a colorless compound, which can be used as a UV stabilizer in applications where yellow color is not required or desired.

THC is a suitable curcuminoid compound, according to some embodiments of the present invention, in applications where yellowish tint is to be avoided.

Curcuminoid compounds can be extracted as naturally occurring substances or be prepared synthetically, and can be used as mixtures thereof or as isolated species. Curcuminoid compounds which are also encompassed by the present embodiments are disclosed in, for example, U.S. Pat. No. 3,479,345, U.S. Patent Application Publication Nos. 20030153512, 20060276536, 20070060644, 20070204412, 20080200478, 20100010232, 20100048901, 20100048901 and 20100087527, all of which are incorporated herein by reference as if fully set forth herein.

It is noted herein that the benefits of incorporating a curcuminoid compound in ophthalmic and ocular devices applies to any polymeric or co-polymeric composition comprising the same. Thus, an ophthalmic or ocular device, according to some embodiments of the present invention, can be made from any suitable polymeric or co-polymeric composition as known in the art, and the curcuminoid compound can be added to the pre-polymerized mixture of the composition before curing, or applied thereon after curing, as described herein.

In some embodiments, the curcuminoid compound is incorporated into the composition as described herein.

As can be seen in the Examples section that follows, the present inventors have successfully incorporated curcumin in an exemplary co-polymeric composition which is suitable for use in ophthalmic and ocular devices, and were able to obtain a desirable level of transparency towards visible light and at the same time opacity with respect to ultraviolet light, using a relatively low concentration of curcumin.

The present inventors have thus demonstrated that naturally occurring (natural) compounds such as curcuminoids, which are generally recognized as safe for human consumption and somatic use, can be used with polymers or co-polymers, such as substantially acrylate-based polymers, to form lasting compositions with suitable UV/blue light blocking and UV-light stabilization properties. The present inventors have shown that using curcuminoids in ophthalmic and ocular devices as blue/UV light blockers may overcome the limitations and possible impairments associated by the use of synthetic compounds such as diphenylazo-based, benzotriazole-based and benzophenone-based UV-blockers and the like.

It has further demonstrated by the present inventors that curcuminoids can be used effectively even at low concentration in a polymeric or co-polymeric composition, relative to the concentration required for benzophenone-based and benzotriazole-based UV-blockers, in order to achieve comparable effective UV-blocking. A low concentration of the UV-blockers not only affects the cost of the resulting product but also affects the visual clarity of the product and its final dimensions. Furthermore, the proven UV-blocking effectiveness of curcuminoids would make it highly suitable in the manufacturing of ophthalmic and ocular devices.

Thus, relatively low concentrations of the curcuminoids are sufficient to exhibit the desired activity. Hence, according to some embodiments of the present invention, the concentration of the curcuminoid compound in the composition ranges from 0.0002 weight percentage to 1 weight percentage or from 0.001 weight percentage to 0.5 weight percentage of the total weight of the composition. Any value lower than 1 weight percent is contemplated, hence any value lower than 0.9, 0.8, 0.7, 0.6, 0.5, 0.4, 0.3, 0.2, 0.1, 0.05, 0.001 and any value lower than 0.0005 weight percent is contemplated as well.

It has been further demonstrated that curcuminoids, unlike many known synthetic phenol-containing UV-blockers, do not inhibit or retard the rate and/or degree of polymerization, when added to the pre-polymerization mixture.

The use of compounds of the curcuminoid family allows selecting a compound with certain optical characteristics, such as, for example, a particular light-absorption range and a particular color or lack thereof.

Without being bound by any particular theory, it is suggested that the transparency of the polymeric or co-polymeric composition is maintained upon incorporating curcumin therein due to the relatively low concentration of the embedded curcumin. Such low concentration is sufficient due to the effective UV-absorption characteristics of curcuminoids and the surprising finding that curcuminoids do not leach out of polymers or co-polymers derived from pre-polymerization mixtures having at least 50 percents acrylic monomers.

As further demonstrated in the Examples section that follows, curcumin was found to be incorporated firmly and consistently in an exemplary polymeric composition, as confirmed by the stability of its concentration in the tested composition before and after the tested composition was subjected to extended cycles of extraction in organic solvents which are known to dissolve curcumin.

As discussed hereinbelow, substances that can leach (be extracted) out of a matrix may cause several adverse effects, such as harming the biological environment (tissue) surrounding the matrix, and reducing the effectiveness of the composition in, for example, blocking UV light. Hence, the characteristic behavior of the curcuminoid in polymeric or co-polymeric compositions can be referred to as low leachability (from the term "leachable") with respect to the matrix constituents and with respect to the curcuminoid compound, and can be defined in terms of comparison of concentrations before and after an extraction process, as this process is discussed hereinbelow.

Low leachability is significant when a substance is used in implantable devices, since in such devices, long-term performance is desired.

The process by which the incorporation of the curcuminoid compound is evaluated is also referred to as the extraction step of unreacted components and diluents (UCDs) from the cured composition, which is discussed in detail hereinbelow, and exemplified in the Example section that follows below.

According to some embodiments of the present invention, there is no perceivable difference in the concentration of the curcuminoid compound after the extraction process for removal of UCDs. Hence, according to some embodiments of the present invention, any of the polymeric or co-polymeric composition described herein as comprising a curcuminoid compound is such that the concentration of the curcuminoid compound in the composition does not decrease as a result of extraction step of UCDs, or decreases by no more than 0.0001%, when subjected to an extraction process in an organic solvent, including also solvents which can readily dissolve the curcuminoid compound.

As discussed herein, a curcuminoid compound can be selected according to the desired light-absorption properties which are required from the composition.

According to some embodiments of the present invention, the curcuminoid can be selected such that the composition is substantially transparent to light at a wavelength ranging from about 400 to about 800 nm, and it can also be selected such that the composition is substantially opaque to light at a wavelength ranging from about 190 to about 440, or substantially opaque to light at a wavelength ranging from about 100 to about 400.

Such optical properties were demonstrated for compositions comprising curcumin, bisdemethoxycurcumin or monodemethoxycurcumin, as the curcuminoid compound.

According to some embodiments of the present invention, the curcuminoid can be selected such that the composition is substantially transparent to light at a wavelength ranging from about 490 to about 800 nm, and it can also be selected such that the composition is substantially opaque to light at a wavelength ranging from about 190 to about 440, or from about 100 to about 490. Such a composition is effective in reducing or essentially blocking the transmission of violet/blue light.

Such optical properties can be afforded when the curcuminoid compound is, for example, tetrahydroxycurcumin (THC).

As discussed herein, UV-light is characterized by a wavelength ranging from 100-440 nm (some sources state that visible region starts from about 390 nm), violet is the color of the short-wavelength end of the human visible spectrum ranging approximately 380-450 nm, and blue light ranges 450-475 nm.

According to some embodiments of the present invention, a polymeric or co-polymeric composition as presented herein, which further comprises at least one curcuminoid compound as described herein is characterized by having UV-light blocking properties, wherein the UV-light is characterized by a wavelength ranging from 100 nm to 440 nm.

Some curcuminoid compounds exhibit yellow color which leads to absorption of visible blue and violet light. According to some embodiments of the present invention, the curcuminoid compound is such that it acts as a UV absorber as well as blue light blocker.

According to some embodiments, two different additives for radiation protection can be present in any of the polymeric or co-polymeric compositions described herein, one for UV-stabilization and another for visible blue light protection.

According to some embodiments of the present invention, any of the compositions described herein as containing a curcuminoid compound can further comprise an additional radiation resistant agent, as described hereinabove.

Combining the beneficial features imparted by the curcuminoid compound as described herein with the beneficial features of the hydrophobic co-polymeric compositions described herein result in a vacuole free, glistening free, internal reflection free and tack free co-polymeric composition, which is protected from the damaging effects of UV light and meet the requirement of tensile strength, deformation recovery ability and mechanical, optical, biological and toxicological requirements.

Processes of Preparing the Polymeric or Co polymeric Compositions:

Any polymeric or co-polymeric composition, according to some embodiments of the present invention, can be prepared by conventional polymerization techniques; however, some processes may be more suitable for ophthalmic or ocular devices.

In general, the compositions are prepared by polymerizing a pre-polymerization mixture as described herein. The pre-polymerization mixture comprises a mixture of monomers, as described herein for the various embodiments of the present invention.

For example, for preparing a co-polymeric composition as described herein, a mixture containing the five types of monomers is used. For preparing a polymeric or co-polymeric composition having a curcuminoid compound incorporated therein or thereon, a mixture containing acrylate monomers as described herein is used.

Incorporation of the curcuminoid compound can be made while adding the curcuminoid compound to the pre-polymerization mixture or by contacting the polymerized (or co-polymerized) composition with the curcuminoid compound and allowing it to be incorporated thereon.

The pre-polymerization mixture can further comprise other optional constituents and additives. Typically, the pre-polymerization mixture further comprises a polymerization initiator such as a free radical polymerization initiator.

According to an aspect of embodiments of the present invention, there is provided a process of preparing a polymeric or co-polymeric composition as presented herein, which is effected by:

admixing a pre-polymerization mixture containing the monomers presented hereinabove, as well as other optional constituents and additives and a free radical polymerization initiator;

optionally degassing the pre-polymerization mixture so as to remove any dissolved gasses which may interfere with optical clarity of the composition by forming vacuoles;

heating said pre-polymerization mixture while stirring;

optionally degassing the pre-polymerization mixture again so as remove volatile residues after heating;

optionally admixing an additional amount of the initiator into the pre-polymerization mixture so as to obtain a polymerization reaction mixture;

admixing a curing agent into the reaction mixture;

casting the reaction mixture into a mold;

exposing the reaction mixture in the mold to curing conditions, to thereby obtain the co-polymer composition presented herein; and subjecting the co-polymeric composition to a multiple extraction so as to rid it from unreacted contaminants.

According to some embodiments of the present invention, the pre-polymerization mixture comprises the first, second, third, fourth, and fifth monomers in their appropriate ratios, as described herein for a hydrophobic co-polymeric composition.

According to some embodiments of the present invention, one of the additives can be a curcuminoid compound, as discussed hereinabove.

Optionally, heating the pre-polymerization mixture while stirring is performed at 40° C. until the viscosity of pre-polymerization mixture reaches an optimal level (120 cps at 25° C.). The viscosity measurements are obtained from the torque applied on the stirring device.

Once all the monomers and other components are mixed together for polymerization, the polymerization reaction may be initiated by adding a radical polymerization initiator in a conventional manner to obtain the polymeric or co-polymeric composition according to some embodiments of the present invention.

The choice of initiator also determines the kinetics of the polymerization reaction. As discussed hereinabove, the molecular weight of the composition confers properties to the ophthalmic device made therefrom, such as glistening, mechanical properties, refractive index and transmittance. Molecular weight is inversely proportional to the half power of the initiator concentration.

The initiator, also referred to herein as a catalyst, is typically employed to initiate the polymerization of the monomers and/or carry out the crosslinking or thermosetting of the polymeric or co-polymeric compositions formed of those monomers, as presented herein. Thus, according to some embodiments of the present invention, the co-polymeric composition present herein further includes an initiator (a catalyst).

According to some embodiments of the present invention, the polymerization reaction follows a free-radical propagation mechanism. As known in the art concerning conventional polymerization methods, the free-radical polymerization reaction may be initiated, for example, by free radical initiators, either thermally or photochemically. When using a thermally initiated free radical polymerization reaction, the method is typically effected by heating gradually from room temperature to an elevated temperature, such as 130° C., and the temperature can be elevated stepwise and/or cycled. When the polymerization initiator is controlled photochemically, the polymerization reaction in initiated by irradiating the pre-polymerization mixture with electromagnetic radiation, such as microwave, ultraviolet light or radiation (y ray) after a radical polymerization initiator is added thereto. It is noted herein that two or more types of initiators may be combined to arrive at a more controlled and completed polymerization reaction.

According to some embodiments of the present invention, the initiation step is effected at relatively low temperatures as a function of the choice of initiator. According to some embodiments of the present invention, the co-polymeric composition includes a low temperature dissociation initiator which keeps the formed device fixed in position in the mold by avoiding significant expansion or contraction. Using such initiators makes the use of fused silica molds redundant, which in turn reduces the need for complex UV-curing of the composition. Hence, according to some embodiments of the present invention, the initiator is a low temperature dissociation initiator.

According to some embodiments of the present invention, non-limiting examples of the initiator include bedicetyl peroxydicarbonate, tert-butyl peroxypivalate, diisobutyryl peroxide, dimyristyl peroxydicarbonate, 1,1,3,3-tetramethylbutyl peroxypivalate, tert-butyl peroxyneoheptanoate, di(2-neodecanoylperoxy-isopropyl)benzene, cumylperoxyneodecanoate, 1,1,3,3-tetramethylbutylperoxy-neodecanoate, t-butylperoxy-neodecanoate, t-butylperoxy-neoheptanoate and any combinations thereof.

According to other embodiments of the present invention, the catalyst is selected from the group consisting of dicetyl peroxydicarbonate (such as Perkadox® 24L by Akzo Nobel Polymer Chemicals, India) and tert-butyl peroxypivalate (such as LUPEROX® 554M75 by Arkema Inc. Philadelphia, Pa., USA).

Non-limiting examples of a radical and/or thermal polymerization initiator include, for instance, azobisisobutyronitorile, azobisdimethylvaleronitrile, benzoyl peroxide, tert-butyl hydroperoxide, qumene hydroperoxide and the like, which can be used solely or in a combination use of two or more thereof.

Light-sensitive initiators (photopolymerization initiator) include, for a non-limiting example, photopolymerization initiators of benzoin compounds such as methyl orthobenzoyl benzoate, methyl benzoyl formate, benzoin methyl ether, benzoin ethyl ether, benzoin isopropyl ether, benzoin isobutyl ether and benzoin n-butyl ether, photopolymerization initiators of phenone compounds such as 2-hydroxy-2-methyl-1-phenylpropane-1-one, p-isopropyl-α-hydroxy-isobutylphenone, p-tert-butyltrichloroacetophenone, 2,2-dimethoxy-2-phenylacetophenone, α,α-dichloro-4-phenoxyacetophenone, and N,N-tetraethyl-4,4-diaminobenzophenone, 1-hydroxycyclohexylphenylketone, 1-phenyl-1,2-propanedione-2-(o-ethoxycarbonyl) oxime, photopolymerization initiators of thioxanthone such as 2-chlorothioxanthone and 2-methylthioxanthone, dibenzosuberone, 2-ethylanthraquinone, benzophenone acrylate, benzophenone, benzil and the like.

The amount of the above-mentioned polymerization initiator is typically not less than 0.002 percent by weight, more preferably 0.01% by weight based on 100% of the total weight of the composition. Alternatively, the concentration of the initiator is not more than 10% by weight, or not more than 2% of the total weight of the composition.

The optional addition of initiator (also referred to herein interchangeably as a catalyst) prior to the casting stage, is meant to boost the completion of the polymerization reaction. As discussed hereinabove, additional initiator is added when the viscosity of the reaction mixture reaches about 120 cps.

According to some embodiments of the present invention, the process includes first adding an amount equivalent to about 20-40% of the total amount of the initiator in the first step of the process, and then adding about 60-80% of the total weight of the initiator.

After mixing and adding the initiator, the mixture is transferred through a filter into the mold. The viscosity at which the mixture is filtered is about 120-130 cps. The ophthalmic device is formed in the mold from the mixture directly into its complete form, avoiding further machining which in turn avoids local burning and machining related stresses. After casting or pouring the mixture in between two halves of the mold, thermal or photo curing stimulus is applied. Thermal curing is performed at room temperature to 80° C. with several ramping steps.

According to some embodiments of the present invention, filtering the reaction mixture may also precede the casting stage.

Once the reaction mixture is cast in a mold, the curing step can start. Exposure to curing conditions typically includes elevating the temperature and/or exposing the reaction mixture to high energy radiation. High temperatures are typically about 80° C., and the irradiation energy may range from 10 KJ/Kg to 50 KJ/Kg in order to further allow the co-polymeric composition to cure.

Curing agents and accelerators may also be employed in the formation of the co-polymeric composition according to some embodiments of the present invention. Various curing agents and accelerators are known and can be used in prescribed amounts or amounts experimentally found to be suitable. Typically, amounts of the curing agent, the curing agent accelerator or a combination thereof are between about 0.1% and about 8% by weight of the total weight of the composition. Curing agents and accelerators can be used in various amounts, which will typically depend upon the monomers and polymers being employed, any ambient conditions (e.g., heat, light or otherwise) being used for curing and/or other factors.

Examples of suitable curing agents include UV photoinitiators, peroxy catalysts (i.e., any catalyst including a peroxy group), oxide catalysts (i.e., any catalyst include an oxide group (e.g., a dioxide) or others known by the skilled artisan. One example of a peroxy catalyst is a tert-butyl peroxy-2-ethylhexanoate organic peroxide initiator, which is particularly suitable for thermal cure. One example of an oxide catalyst is 2,4,6-trimethylbenzoyldiphenylphosphine oxide, which is particularly suitable for blue light cure.

According to some embodiments of the present invention, the monomers, the initiator, the curing agent and optionally curing agent accelerator, a UV-blocker (radiation resistant compound), if present, and any other desired ingredients are combined together to form a master batch. The master batch is then exposed to an ambient stimulus, such as heat or light (e.g., blue light) which initiates polymerization and cross-linking reactions between the various monomers. The initiated master batch can be cast into molds (such as cast wafers) of desired geometry and can be secured in cure fixtures for forming the ophthalmic devices. It is advisable to add a crosslinking monomer in initial stage especially in the case where the polymerization reaction is performed at relatively low temperature.

The wafer molds are then typically cured through extended exposure to an ambient condition such as heat, light or both. For example, in one embodiment, the cast wafers are exposed to an elevated temperature (e.g., about 70° C.) for a first period of time (e.g., about 2 hours) and then ramped up to a second temperature (e.g., about 110° C.) for a second period of time (e.g., at least 10 minutes). In a second exemplary embodiment, the wafers are cured using blue light at a wavelength of about 405 nm to about 415 nm for a first period of time (e.g., about 3 hours) and then exposed to an elevated temperature (e.g., about 110° C.) for a second period of time (e.g., about one hour). Typically, the initiation, the curing or both are carried out in a low moisture (e.g., less than 1 ppm water) and low oxygen (less than 100 ppm) environment.

Alternatively, working at relatively low temperatures, from room temperature and up to 80° C. is advantageous, since it allows the polymerization and curing steps to complete post the casting stage (namely in the mold), without causing thermal distortion of the mold. This way a relatively low cost polypropylene mold can be used, instead of a costlier fused silica molds.

During the initial polymerization step it is possible to monitor the viscosity of the master batch mixture, for example by following the force applied to the mixing shaft.

Once the polymeric or co-polymeric composition is cured it can be cleansed from unreacted components and other leachables. The extraction of leachables may commence once the molded and cured composition is released from the mold. According to some embodiments of the present invention, the extraction is effected by sequential immersion of the polymeric or co-polymeric composition in a series of baths, each containing a different solvent or solution, going from hydrophobic to hydrophilic in the order of sequence, thereby extracting unreacted contaminants from the composition.

Following the description of the embodiments of the present invention, provides polymeric and co-polymeric compositions and processes for preparing the same, which are highly suitable for manufacturing implantable and non-implantable ophthalmic and ocular devices. Following the above-described description of the embodiments affords vacuole free, glistening free, internal reflection free and tack free ophthalmic and ocular devices, which meet the requirement of tensile strength, deformation recovery ability and mechanical, optical, biological and toxicological requirements set by widely accepted standards of the art.

It is noted that even after the post-curing step, which further pushes the polymerization reaction to completion, some impurities from unreacted monomers and other contaminants remains in the composition. These impurities are commonly referred to herein as unreacted components, diluents and other leachable impurities. Under the term leachable impurities are also included filter membrane residues, boiling impurities, solvent remnants and other process contaminants.

To remove unreacted components and diluents (UCDs) and other leachable impurities from the cured composition, and affect clinical viability of the device, the process of preparing such devices typically includes an extraction step. If the leachable substances are not extracted from the device, they may make the device uncomfortable to wear or even present a medical hazard. As used herein, "leachable substance" includes UCDs and other substances which are not bound to or embedded in the polymer and may be extracted from the composition (the matrix), for example, by leaching with water or an organic solvent. As used herein, the term "treat" means to expose a cured object or device, made from the composition presented herein, to an aqueous and/or organic solution which may also include at least one leaching aid. Treating a cured polymeric composition to remove UCDs and monitoring traces thereof is demonstrated in the Examples section which follows below using a curcuminoid compound as a light-stabilizer, which is not part of the polymeric backbone and therefore required not to leach out of the cured composition.

As used herein, a "leaching aid" is any compound that if used in an effective amount in an aqueous or organic solution to treat an ophthalmic device, and can assist in obtaining a device with an adequate amount of removal of leachable substances.

According to embodiments of the present invention, the process of preparing the co-polymeric composition presented herein may include a treatment of the cured co-polymeric composition. The treatment step can include exposing the cured composition to an aqueous and/or organic solution which constitutes or includes at least one leaching aid. In various embodiments, treatment can be accomplished, for example, via immersion of the device in a solution or exposing the device to a flow of solution or exposing the device to Soxhlet extraction. In various embodiments, treatment can also include, for example, one or more of heating the solution; stirring the solution; mechanical agitation or sonication of the solution; and increasing the level of leach aid in the solution to a level sufficient to facilitate adequate removal of leachable substances from the device.

According to some embodiments of the present invention, an organic or aqueous solution may constitute a leaching aid. According to other embodiments of the present invention, leaching aids can also be combined with organic solvents to improve the rate of release. For example, in some embodiments, ophthalmic devices such as lenses can be subjected to a treatment exposing the lens devices to a leaching aid and a GC Mass Spectrometer can be used to measure the level of one or more leachable substances in the lens devices. The GC Mass Spectrometer can determine whether treatment with a particular leaching aid is effective to reduce an amount of particular leachable substances present in the lenses to a maximum threshold amount. Accordingly, in some embodiments, a GC Mass Spectrometer can be used to check for a maximum threshold of leachable substances of approximately 300 ppm. A minimum hydration treatment time period necessary to reduce the presence of such leachable substances to 300 ppm or less in specific lenses can be determined by the periodic measurements. In additional embodiments, other leachable substances, such as, for example, D30 or other diluents, can be measured to detect the presence of a maximum amount of approximately 60 ppm. Embodiments can also include setting a threshold amount of a particular leachable substance at the minimum detection level ascertainable by the testing equipment.

Examples of leaching aids, according to the present invention include, without limitations, alkanes, ketones (e.g. 2-butanone), amides, ethers (e.g. THF), alcohols (e.g. methanol), esters (e.g. ethyl acetate), aldehydes, nitrogen-containing cyclic compounds, toluene, water, ethoxylated alcohols or ethoxylated carboxylic acids, ethoxylated glucosides or sugars, optionally with attached $C_6$-$C_{14}$ carbon chains, polyalkylene oxides, sulfates, carboxylates or amine oxides of $C_6$-$C_{14}$ compounds. Examples include cocamidopropylamine oxide, $C_6$-$C_{14}$ fatty alcohol ethoxylated with ethylene oxides, sodium dodecyl sulfate, polyoxyethylene-2-ethyl hexyl ether, polypropylene glycol, polyethylene glycol monomethyl ether, ethoxylated methyl glucoside dioleate, and the sodium salt of n-octylsulfate, sodium salt of ethylhexyl sulfate.

By way of non-limiting examples, various implementations can include release and removal of leachable impurities that is accomplished by way of a batch process wherein devices are submerged in a solution contained in a fixed tank for a specified period of time or in a vertical process where devices are exposed to a continuous flow of a solution that includes at least one of a leach aid. In some embodiments, the solution can be heated with a heat exchanger or other heating apparatus to further facilitate leaching of the device. For example, heating can include raising the temperature of an aqueous or organic solution to the boiling point while a device is submerged in the heated solution. Other embodiments can include controlled cycling of the temperature of the solution. Some embodiments can also include the application of physical agitation to facilitate leach. For example, a strainer container holding the device can be vibrated or caused to move back and forth within a leaching solution. Other embodiments may include ultrasonic waves through the solution.

The choice of a leaching aid or solvent depends on the impurities present in the composition. Each solvent has a capability of extracting certain impurities with an overlapping range of chemical efficiency. For example, 2-butanone, THF, methanol and ethyl acetate are used sequentially on a same set of fully cured devices; which helps in removing all identified impurities step by step. Water miscible solvents are kept for last. A continuous soxhlet extraction may be employed which utilizes fresh solvent each time. Each soxhlet extracting phase may be sized to hold 500 lenses of 20 diopter. Maximum quantity varies with the power for given sized extractor. However extractors can be easily scaled up to meet the quantity requirement. Flow rate for the solvent varies according to extractor and according to cycle time. A holding time of 3 hours is kept for each solvent. For example, a drop rate of 100 ml/hr is kept for 300 ml extractor.

For example, freshly cured ophthalmic or ocular devices, prepared from the polymeric or co-polymeric composition presented herein, are kept in glass thimble, which is soaked in a bath of one leaching aid solution, and then exchanges its position to a bath holding the next solvent and so on; wherein each soak is maintained for 15-30 minutes. A vacuum tempering is performed thereafter in order to dry the devices at 110° C. and 0.1 mbar.

According to some embodiments of the present invention, post operation of reducing tack may be performed on a anterior surface or on both surface by processing lens by methods such as plasma treatment, surface fluorination, bulk fluorination, hydrophilic coating, irradiating with EB rays, high energy UV rays or by other energy intensive rays, use of internal wetting agents for selective migration and allied.

Ophthalmic Device Made from Polymeric or Co-Polymeric Compositions:

The polymeric or co-polymeric composition as described herein, optionally having a curcuminoid compound incorporated therein or thereon as described hereinabove, can be used to form any ophthalmic or ocular device.

Any ophthalmic or ocular device, typically a lens, formed from any of the compositions presented herein, can be manufactured by using one or two basic methods: molding into a final form without further machining, and shaping and molding followed by machining for reshaping and polishing. Hence, a device as described hereinbelow, made from a polymeric or co-polymeric composition as presented hereinabove, can be made while preparing the polymeric or co-polymeric composition, or prepared from a pre-formed polymeric or co-polymeric composition.

For example, multi-part molds can be used to fashion the composition presented herein into a useful article of a complex shape, such as an ophthalmic device or any other type of lens. In the case of a lens, the multi-part molds can include for example, a first mold part with a convex or concave surface that corresponds to a back curve of an ophthalmic lens, and a second mold portion with a generally convex surface that corresponds to a front curve of the lens. To prepare a lens using such mold portions, the uncured lens' composition is placed between the mold portions and subsequently cured. The lens' composition may then be cured, for example by exposure to either or both heat and light. The cured composition forms a lens body according to the dimensions and features of the mold portions. Following curing, traditional practice dictates that the mold portions are separated and the lens remains adhered to one of the mold portions, calling for a release process to detach the lens from the remaining mold part. In some embodiments, the process of manufacturing the lens body, the cured lens body may be subjected to further polishing and/or shaping to achieve final desired form.

The formation of the ophthalmic device from the composition presented herein can also be effected by, for example, a computer-controllable manufacturing device. For example, the ophthalmic or ocular device presented herein may be shaped into final form in two basic steps, wherein in the first step the crude lens is forged from the co-polymeric composition presented herein, and in the second step other structural features are formed in the cured crude lens body using a computer controllable manufacturing device.

A "computer controllable manufacturing device" refers to a device that can be controlled by a computer system and that is capable of producing directly a lens body or a mold for producing an ophthalmic device. Any known, suitable computer controllable manufacturing device can be used in the invention. Exemplary computer controllable manufacturing devices include, but are not limited to, lathes, grinding and milling machines, molding equipment, and lasers. In various exemplary embodiments of the invention a Computerized Numeric Controlled (CNC) lathe machine can be used, such as the lathers marketed under the trade names DAC™ Vision, Optoform and Care Tec.

Some ophthalmic and ocular devices, formed from any of the compositions presented herein, may require different techniques and protocols known in the art.

According to an aspect of some embodiments of the present invention there is provided an ophthalmic device comprising any of the polymeric or co-polymeric composition presented herein.

It is noted herein that the polymeric or co-polymeric compositions presented herein containing a curcuminoid compound may constitute any ophthalmic or ocular device, such as a lens, that is prepared therefrom. The polymeric and/or co-polymeric compositions described herein confer the refractive index, strength, transparency, vacuoles, halos, UV-stabilization and other traits, characteristics and parameters, to the products made therefrom.

In some embodiments of this aspect, a composition as described herein is formulated for insertion into or onto an eye, namely it is required to be bio-compatible, chemo-compatible and physico-compatible in order to be used in an ophthalmic device.

The present embodiments also contemplate a method of treating vision of a subject in need thereof using any ophthalmic or ocular device made from any of the compositions described herein. The method is effected by inserting, applying and/or implanting the ophthalmic or ocular device in an eye of the subject, thereby treating the vision of the subject. The method can be exercised, for example, while or subsequently to a cataract surgery. The devices disclosed herein can be beneficially used to correct standard optical distortions and in the treatment of ophthalmic conditions, such as for example, retinal detachment; occlusions; proliferative retinopathy; proliferative vitreoretinopathy; diabetic retinopathy; inflammations such as uveitis, choroiditis, and retinitis; degenerative disease (such as age-related macular degeneration, also referred to as AMD); vascular diseases; and various tumors including neoplasms.

The devices may take the form of a multifocal ophthalmic device, a monofocal ophthalmic device, a contact lens, an implantable ophthalmic device, an intraocular lens (IOL), a keratoprosthesis, a phakic lens, an aphakic lens, a corneal ring, a capsular bag extension ring, a corneal inlay and a corneal onlay may be used in the treatment of an optical distortion, a retinal detachment, an occlusion, proliferative retinopathy; proliferative vitreoretinopathy, diabetic retinopathy, a degenerative disease and an age-related macular degeneration.

It should be noted herein that according to some embodiments of the present invention, any of the compositions presented herein can be used to manufacture ophthalmic devices used also for drug delivery. In these embodiments, the non-leachability of the main additives and components (such as, for example, the curcuminoid compound discussed hereinabove) is in effect, however, the drug which is delivered from the device to the surrounding tissue is in fact leachable, and can diffuse from the matrix (typically a hydrogel) to the physiological medium in which the device is situated and from there to the tissue to be treated.

Additional features of the ophthalmic device, co-polymeric composition and/or polymeric or co-polymeric composition incorporating a curcuminoid therein are described in International Patent Application No. IB2010/053818 and in Indian Patent Application Nos. 1938/MUM/2010 and 2888/Mum/2010, the teachings of which are incorporated by reference as if fully set forth herein.

It is expected that during the life of a patent maturing from this application many relevant polymeric and co-polymeric compositions, with and without curcuminoid compounds, for ophthalmic and ocular devices will be developed and the scope of such compositions is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" in the context of a medical condition, includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "treating" in the context of an object undergoing an industrial and/or mechanical and/or technical process, includes improving, refining, or otherwise advancing the progression of the process with respect to the object.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following example.

EXAMPLES

Reference is now made to the following example, which together with the above descriptions illustrates some embodiments of the invention in a non limiting fashion.

Example 1

Co-Polymeric Composition—Materials and Methods 2-phenoxyethyl acrylate (POEA) was obtained from Sigma-Aldrich, India, and used as an exemplary aromatic monomer characterized as forming a homopolymer having a refractive index of that ranges from 1.50 to 1.53 (first aromatic acrylate monomer).

2-phenylethyl acrylate (PEA) was obtained from Polysciences Inc., and used as an exemplary aromatic monomer characterized as forming a homopolymer having a Tg lower by 2-30° C. than a Tg of the homopolymer of POEA (second aromatic acrylate monomer).

2-methoxyethyl methacrylate (MOEMA) was obtained from Sigma-Aldrich, India, and used as an exemplary monomer characterized as forming a homopolymer having a Tg lower than 35° C. (third monomer).

The above monomers were used after high vacuum distillation for removal of polymerization inhibitors and impurities such as corresponding alcohols and acid.

2-hydroxyethyl methacrylate (HEMA) was obtained from Sigma Aldrich, India, and used as is, as an exemplary monomer characterized as forming a homopolymer which is capable of absorbing water to at least 20% of its total weight (fourth monomer).

1,4-butane diol diacrylate (BDDA) was obtained from Sartomer, Asia, and used as is, as an exemplary crosslinking monomer. The incorporation of a crosslinking monomer depends on the intended/desired unfolding time, flexibility, loop pull force and compression force. This exemplary crosslinking monomer is being selected as suitable in the development of an IOL which requires a short unfolding time of less than or equal to 5 seconds (fifth monomer).

2,2'-azobis-(2,4-dimethylvaleronitrile) (AIVN) was obtained from HPL Polymer Additives, India, and used as is, as an exemplary initiator.

2-(5-chloro-2H-benzotriazole-2-yl)-6-(1,1-dimethylethyl)-4-methyl-phenol (TINUVIN® 326) was obtained from Ciba Specialty Chemicals, India, and used as is, as an exemplary UV absorber of the hydroxyphenylbenzotriazole class.

4-[(E)-phenyldiazenyl]-phenyl-2-methacrylate was synthesized in the inventor's laboratory, and used as an exemplary yellow dye.

Refractive Index:

The refractive index of some exemplary polymeric compositions presented hereinbelow was determined following the ASTM D542-2000 standard using an Abbe refractometer prisms system (ATAGO U.S.A., Inc, Model DR-A1).

Tested specimens are cut to blocks of 1 mm thickness, 10 mm width and 50 mm length. The blocks are fitted on the face of the fixed half of the refractometer prisms system. Both surfaces are polished to the extent that sharply defined straight dividing line is seen. Three specimens are prepared for each batch of polymeric composition. Conditioning is done at 23±2° C. and 50±5% relative humidity for no less than 40 hours prior to test, and the test is conducted at same conditions.

Mechanical Strength:

The mechanical strength (also referred to herein interchangeably as the "loop pull force") of some exemplary polymeric compositions presented hereinbelow was determined following the ISO 11979-3:2006 standard using a standard tensometer (Universal Testing Machine, Lloyd's LF plus with 10N load cell).

Lenses prepared from polymeric compositions according to some embodiments of the present invention, were conditioned at 23±2° C. and 50±5% relative humidity for not less than 40 hours prior to testing, and the tests were conducted at same conditions.

The lenses were clamped so that the direction of the pull was tangential to the loop at the loop/optic junction in the tensometer. The extension rate was set at 1 mm/minute and the tensometer was activated. The lens was pulled until the loop broke or separates from the lens and the Young's modulus value recorded.

Glass Transition Temperature (Tg):

The glass transition temperature of some exemplary polymeric compositions presented hereinbelow was determined following the ASTM D3418-03:2000 standard using a differential Scanning colorimeter (Shimadzu Scientific Instruments, Model DSC 60A).

Polymeric composition specimens' mass was 15 mg. Helium was purged during weighing and testing, and the weighing was performed at an accuracy of ±10 μg.

A preliminary thermal cycle was performed and recorded by cooling the sample at a rate of 20° C. per minute from at least 37° C. to −50° C. The temperature was maintained for five minutes at 37° C. and thereafter quenched to −50° C. and maintained at that for five minutes. This cooling cycle was repeated at a rate of 20° C. per minute and the cooling curve was recorded until distinct lineaments of glass transition temperature have been completed.

Shore A Hardness:

The Shore A hardness of some exemplary polymeric compositions presented hereinbelow was determined following the ASTM D2240:2000 standard using a digital Shore A hardness meter (Mitutoyo America Corporation, Model HH-336-01).

Digital Shore A hardness meter was attached to a constant pressure hardness measurement stand. A sample of a polymeric composition, according to some embodiments of the present invention, was placed exactly within the shaped cavity, and a side lever was pressed until the reading of the pressure gauge was constant, and the Shore A hardness value was recorded.

Visible Light Transmission:

The visible light transmission of some exemplary polymeric compositions presented hereinbelow was determined following the ASTM D 1003 standard and using a visible light spectrophotometer (Varian, Inc., Model Cary 50).

Samples of the polymeric composition according to some embodiments of the present invention, were cut to blocks of 1 mm thickness, 10 mm width and 50 mm in length so as to fit into the polished face of a quartz cuvette. Both surfaces of the sample were polished to the extent that no gap is seen between the cuvette surface and sample. Such highly polished surface, typically to an IOL, is needed to minimize the losses due to air interface scattering. Three samples were prepared from each preparation batch, and conditioned at 23±2° C. and 50±5% relative humidity for at least 40 hours prior to testing, and testing was conducted at same conditions.

The spectrum of the test was set from 250 nm to 800 nm in UV-Vis spectrophotometer panel, and the sample was scanned through the whole spectrum of wavelengths while recording the transmission results.

Unfolding Time:

The unfolding time of the finished lens product, prepared from polymeric compositions according to some embodiments of the present invention, was determined using an injector, a cartridge and a stopwatch.

A 1.85 mm diameter sterile cartridge was filled with Visco elastic (Viscolon) solution or another suitable delivery medium, and the tested lens was placed in by means of forceps. The lens was put into the cartridge folded while letting the interior surfaces come in contact. The cartridge was loaded into the injector, and excess Viscolon was forced out of the cartridge. The injector plunger was pressed smoothly so as to force the lens comes out of the cartridge onto a Petri dish which filled with 0.9% saline at 25° C.

The exact time interval for unfolding was recorded with a precise stop watch, started from the point when the lens comes out of cartridge and up to the point when it is completely relaxed in the saline and unfolds fully, and this time interval was defined as the unfolding time for a particular lens sample.

Glistening Test:

The glistening of the finished lens product, prepared from polymeric compositions according to some embodiments of the present invention, was determined using a microscope.

The lens was immersed in physiological medium such as 0.9% saline solution, and kept at 40° C. in forced air circulatory oven for 72 hours. The lens was thereafter cooled while immersed in the saline for a period of 3 hours, and thereafter observed under a 50× microscope for examination for vacuoles and glistening.

Extractables and Leachables Content:

The extractables and leachables content (also referred to herein as the leachable content) in samples of the polymeric composition according to some embodiments of the present invention, was determined following the ISO 11979-5:2006 and ISO 11979-5:2006 standards and using standard gravimetric analysis.

A number of exemplary lenses were dried under vacuum at 60° C.±5° C. for three hours, and thereafter allowed to cool to room temperature under vacuum before weighing. The lenses were weighed to the nearest 0.1 mg and placed in an extraction thimble. Boiling stones were placed in the flask, and the flask was filled to about 50% of its capacity (about 250 ml) with THF.

The extraction thimble was placed in a Soxhlet apparatus fitted with the flask and a condenser. The flask was heated with a mantle and while chilled water was circulated through the condenser. The extraction rate was set at about 4 thimble flushes per hour and the lenses were extract for 3 hours.

At the end of the extraction cycle the solvent was allowed to cool to room temperature and the thimble with the lenses was removed from extractor. The lenses were put in a Petri dish under laminar flow, and carefully separated from each using PTFE coated forceps. The extracted lenses were dried to constant mass in a vacuum oven.

The total weight of the dried lenses was determined after the first extraction cycle and the change in weight effected by the extraction was recorded. The procedure was repeated with methyl ethyl ketone and methanol respectively with new thimbles.

Dioptric Power:

The resulting dioptric power was compared to the expected dioptric power following the ISO 11979-2:1999 standard and using a standard dioptric power measuring device (ROTLEX Ltd., Israel, Model IOLA Plus).

The expected dioptric power was determined using dimensionally details pertaining to the casting halves of the mold. Such a test can identify uneven or greater shrinkage in the cast which may lead to unacceptable optic parameters or variation in the dioptric power, leading to disqualification of a lens product. A process of extraction mainly contributes to the uneven shrinkage.

The pre-polymerization mixture of the polymeric composition according to some embodiments of the present invention, was cast in mold halves and processed subsequently to form an IOL.

The power of the lens was measured at the end of process and recorded together with the difference in the expected dioptric power.

Tackiness:

The tackiness of the finished lens product was determined following ASTM D 3654 standard and using a standard tensometer (Universal Testing Machine, Lloyd's LF plus with 10N load cell).

A tested polymeric composition was formed and cast as a lens but in a form of strips having dimension 50 mm in length, 10 mm in width and 1 mm in thickness.

Posterior surface of two strips were faced towards each other and pressed by 200 gm weight for 24 hour at 25° C., thereby forming a single lap shear joint. 10 mm edges were left unattached at either end of the strips intentionally. These ends were used for gripping in a fixture attached to universal testing machine (mechanical testing machine).

Thereafter the joint strips were vertically aligned and stretched at constant rate of elongation of 2 mm per minute.

A peak force reading point of break was recorded. This was determined as the shear force required to separate the joint strips which, and assign as the measure of tackiness or self adhesion integrity.

Modular Transfer Function:

The modular transfer function (MTF) of some exemplary polymeric compositions presented hereinbelow was determined following the ISO 11979-2:1999 standard and using a standard model eye (ROTLEX Ltd., Israel, Model IOLA Plus).

Samples of IOL, prepared from the polymeric composition according to some embodiments of the present invention, was placed in cuvette filled with saline and a converging beam from the model cornea exposed the central circular 3.00 mm±0.1 mm of the lens. The difference in refractive index between the lens and the liquid medium was recorded within 0.005 units of that under in situ conditions.

The lens front surface was placed at a plane between 27 mm to 28 mm in front of the focal point of the model cornea itself, taking refractive index of the image space to be 1.336. The light source was by filtration or otherwise confined to 546 nm±10 nm.

The procedure was performed while ensuring that the lens is in the correct position, and that the whole unit is well aligned with the optical axis of the bench, and focused to obtain maximum MTF at 100 lines per millimeter while recording the MTF value.

Example 2

Polymerization Mixture and Reaction

Following are formulations and a process for forming an exemplary polymeric composition, according to some embodiments of the present invention.

General Procedure:

Prior to weighing, all monomers are degassed for 30 minutes in a degasser operating at 50 mm Hg vacuum.

All monomers, initiator, UV absorber and yellow dye are mixed in a reaction kettle at room temperature until the liquid mixture becomes homogenous and clear.

After blending, nitrogen is purged for 15 minutes by bubbling though the mixture, and the mixture is added to a stirred autoclave reactor and heated to 40° C. while stirring with a three-blade propeller under a 2 Kg nitrogen pressure.

When the amount of unreacted volatile matter drop below 30% w/w and the viscosity reach 120±10 cps at 25° C., the reaction mixture is cooled to −30° C. in an oil bath, and thereafter is allowed to warm up to room temperature.

Thereafter additional initiator is added to the reaction mixture while mixing the mixture until all the initiator is fully dissolved.

Preparation of an Exemplary Composition:

Exemplary co-polymeric composition, denoted Ex. 0 hereinafter, was prepared as follows.

Prior to weighing, all monomers were degassed for 30 minutes in a degasser operating at 50 mm Hg vacuum. The exemplary formulation presented below represents a batch size of 600 grams.

342 grams of 2-phenoxyethyl acrylate, 102 gm of 2-phenyl ethyl acrylate, 90 grams of 2-methoxyethyl methacrylate, 54 grams of 2-hydropxyethyl methacrylate, 12 grams of 1,4-butane diol diacrylate, 0.3 grams of 2,2'-azobis(2,4-dimethylvaleronitrile), 1.2 grams of TINUVIN® 326 (benzotriazole UV absorber) and 0.72 grams of 4-[(E)-phenyldiazenyl]-phenyl-2-methacrylate (yellow dye) were added to a 1 liter reaction kettle, and mixed at room temperature until the liquid mixture became homogenous and clear.

After blending, nitrogen was purged for 15 minutes by bubbling though the mixture, and the mixture was added through an addition funnel to a stirred autoclave reactor and was heated to 40° C. while stirring with a three-blade propeller under a 2 Kg nitrogen pressure. The solution became gradually viscous while monomer entities turn to high molecular weight chains.

When the amount of volatile matter, mainly unreacted monomer entities and short oligomers, had dropped below 30% w/w, as required by the ASTM D 1353-09 standard, and the viscosity has reached 120±10 cps at 25° C., as determined by measuring torque experienced by stirrer shaft connected to constant RPM motor, the reaction mixture was cooled to −30° C. in an oil bath, and thereafter allowed to warm up to room temperature.

Thereafter 1.2 grams of the initiator 2,2'-azobis(2,4-dimethylvaleronitrile) were added to the reaction mixture while mixing the mixture until all the initiator was dissolved therein.

The above exemplary polymeric composition, referred to herein as "Ex. 0", was prepared from the exemplary formulation presented above, having the following proportions:

POEA—56%;
PEA—17%;
MOEMA—15%;
HEMA—9%;
BDDA—2%;
AIVN—0.05% initial aliquot plus 0.2% second aliquot;
UV absorber—0.2%; and
Yellow Dye—0.12%.

The final homogenous mixture of Ex. 0 was filtered through 0.2 micron PTFE membrane disc filter and placed into a dosing pump.

Example 3

Intraocular Lens Product Molding and Post-Molding Workup

The polymerization mixture was prepared as described hereinabove, a curing agent was added thereto and the mixture was dispensed into intraocular lens polypropylene mold halves.

The mixture was cured in a temperature cycle of 40° C. for 12 hours; 45° C. for 6 hours; and 50° C. for 6 hours.

As discussed hereinabove, intraocular lenses, prepared as described hereinabove, may contain impurities such as un-reacted monomers, crosslinker, initiator and other residues, which may leach out into the physiological aqueous media once implanted in the eye. In order to cleanse the product, a multi-solvent extraction procedure was used to remove these impurities as described below.

About 30 intraocular lenses were placed in an immersible lens mount fitted to a 60 ml extractor vessel (obtained from Sigma Aldrich, India). The extractor vessel was filled with an alcohol such as isopropanol, and the lenses were kept therein under reflux temperature for 9 hours. This procedure was repeated using a ketone such as acetone. Thereafter the lenses were dried in a vacuum oven at 10 mm of Hg and 110° C.

After drying, the cleansed lenses were treated with EB rays (electron beam) to quench unreacted monomers and reduce tack on the interior and exterior surfaces.

Example 4

Additional Formulations

Lens products made from other exemplary formulations for polymeric compositions, according to some embodiments of the present invention, were prepared by following the aforementioned procedures for preparation of the pre-polymerization mixture, polymerization reaction, molding and post-molding workup.

Table 1 presents additional exemplary formulations for polymeric compositions according to some embodiments of the present invention, wherein the resulting compositions are denoted Ex. 1-10, and each component is presented in its relative content in weight percentage of the total weight of the composition.

TABLE 1

| Component | POEA | PEA | MOEMA | HEMA | BDDA | AIVN | UV absorber | Yellow Dye |
|---|---|---|---|---|---|---|---|---|
| Ex. 0 | 56 | 17 | 15 | 9 | 2 | 0.25 | 0.2 | 0.12 |
| Ex. 1 | 16 | 57.5 | 15 | 8.85 | 2.65 | 0.25 | 0.2 | 0.01 |
| Ex. 2 | 67.65 | 18.82 | 0 | 10.41 | 3.12 | 0.25 | 0.2 | 0.01 |
| Ex. 3 | 68.5 | 0 | 17.85 | 10.5 | 3.54 | 0.25 | 0.2 | 0.01 |
| Ex. 4 | 0 | 37.65 | 35.3 | 20.82 | 6.23 | 0.25 | 0.2 | 0.01 |
| Ex. 5 | 63.1 | 17.55 | 16.46 | 0 | 2.91 | 0.25 | 0.2 | 0.01 |
| Ex. 6 | 59.06 | 16.43 | 15.41 | 9.1 | 0 | 0.25 | 0.2 | 0.01 |
| Ex. 7 | 52.5 | 16 | 11 | 7 | 2 | 0.25 | 0.2 | 0.06 |
| Ex. 8 | 54.5 | 17 | 12 | 7.5 | 2.5 | 0.25 | 0.2 | 0.06 |

TABLE 1-continued

| Component | POEA | PEA | MOEMA | HEMA | BDDA | AIVN | UV absorber | Yellow Dye |
|---|---|---|---|---|---|---|---|---|
| Ex. 9 | 56.5 | 18 | 13 | 8 | 3 | 0.25 | 0.2 | 0.06 |
| Ex. 10 | 58.5 | 19 | 14 | 8.5 | 3.5 | 0.25 | 0.2 | 0.06 |

Example 5

Analyses and Characterization of Ophthalmic Co-Polymeric Composition

The resulting lens products, prepared according to the procedure presented hereinabove, were tested for a series of characteristics, and analyzed according to industry-accepted parameters, as presented herein.

Following are the quality test results obtained for exemplary composition Ex. 0 prepared as described in Example 1 hereinabove:

Refractive index: 1.525;
Loop pull Force (mechanical strength): 45 grams;
Glass transition temperature (Tg): 9° C.;
Shore A hardness: 78;
Visible light transmission: more than 98%;
Unfolding time at 25° C. in 0.9% saline: 5 Seconds;
Visual glistening test: Substantially free of glistening and vacuoles;
Percent extractables/leachables: 0.3%
Resulting dioptric power versus expected resultant power: 20D versus 20D;
Tack after EB treatment: tack free; and
Modular transfer function: 0.68.

The characteristics obtained from the aforementioned tests, for exemplary polymeric compositions according to some embodiments of the present invention, and lenses made therefrom, produced as described hereinabove from the aforementioned exemplary polymeric compositions presented in Example 4, Table 1, are presented in Table 2 below.

The test denoted "1" presents the refractive index as measured at 25° C.; The test denoted "2" presents the vacuoles presence as measured in water at 25° C.;

The test denoted "3" presents the Shore A hardness ratios;

The test denoted "4" presents the visible light transmission, given a positive score when accomplishing less than 1% transmission of visible light at 370 nm, more than 70% transmission at 400 nm, and a 10% cut-off in the wavelength range of 370-380 nm;

The test denoted "5" presents the unfolding time at 25° C. in normal saline through sub 2 mm cartridge;

The test denoted "6" presents the halo's test (internal reflection) results in dry conditions, given a positive score if no internal reflection can be detected;

The test denoted "7" presents the percent of detectable leachables after post-molding operation; and The test denoted "8" presents the tack feel, given a positive score if no tackiness can be perceived.

TABLE 2

| TEST No. | 1 | 2 | 3 | 4 | 5 | 6 | 7 | 8 |
|---|---|---|---|---|---|---|---|---|
| Ex. 0 | 1.525 | clear | 78 | + | 5 | + | 0.3 | + |
| Ex. 1 | 1.5371 | clear | 76.8 | + | 2 | − | 0.62 | − |
| Ex. 2 | 1.5466 | opaque | 81.7 | + | 6 | + | 0.78 | − |
| Ex. 3 | 1.5354 | hazy | 81.8 | + | 2 | + | 0.59 | − |
| Ex. 4 | 1.5069 | opaque | 85.8 | + | 2 | + | 0.47 | + |
| Ex. 5 | 1.5328 | opaque | 81.3 | + | 3 | + | 0.65 | − |
| Ex. 6 | 1.5265 | translucent | 74.8 | + | 9 | + | 1.3 | −/+ |
| Ex. 7 | 1.52 | clear | 80 | + | 5.14 | + | 0.42 | −/+ |
| Ex. 8 | 1.522 | clear | 79.7 | + | 5.6 | + | 0.48 | −/+ |
| Ex. 9 | 1.525 | clear | 78.6 | + | 4.8 | + | 0.49 | −/+ |
| Ex. 10 | 1.527 | clear | 78 | + | 4.4 | + | 0.47 | −/+ |

As can be seen in Table 2, the results obtained for the exemplary polymeric compositions according to some embodiments of the present invention, clearly show superior characteristics by industry standards, wherein the polymeric compositions denoted Ex. 0 and 7-10 exhibit optimal performance.

Example 6

Curcumin Sample Preparation

Materials and Experimental Methods:

Silica Gel 60 aluminum plates, and preparative Silica gel 60 extra pure for column chromatography 0.063-0.200 mm (70-230 mesh), were obtained from Merck KGaA, Germany.

A commercially available mixture of curcuminoids (Sigma Aldrich, India; Product number C1386; 70% curcumin purity) was post purified to at least 97% curcumin as follows. Preparative silica gel was used to fill a prefabricated column, and a mixture of curcuminoids (1% concentration in acetone) was loaded and eluted through the column at 25° C. using a mixture of chloroform and ethyl acetate (9:1 ratio).

The solvent was removed by vacuum distillation to afford a residue. The solid residue was dried in a vacuum oven at 50° C. under 0.1 mbar for 3 hours.

Assay and purity of curcumin was conducted by measuring melting point and λmax on UV-Vis spectrophotometer. The melting point of the solid residue was measured at 181° C. (published meting point for curcumin is 182-183° C.), and the λmax was found to be 419 nm (within range 415-420 nm as the published λmax for curcumin at concentration of 10 mg/l in acetone).

FIG. 1 presents the UV-Vis absorption spectra of the sample of curcumin after purification on a preparative silica gel column at 25° C. using a mixture of chloroform and ethyl acetate (9:1 ratio).

The impurities may be attributed to monodemethoxycurcumin, and bisdemethoxycurcumin, whose boiling point and color differs significantly from curcumin (reported boiling point of bisdemethoxycurcumin is 232-233° C.).

Example 7

Transparent Polymeric Object Containing Curcumin

Materials and Experimental Methods:

Dilauroyl peroxide (Cat. No. 34974) was obtained from Acros Organics.

4-[(E)-phenyldiazenyl]phenyl-2-methacrylate (PDPMA) was obtained from local contract laboratories.

The acrylic monomers 2-Phenoxy ethyl methacrylate (POEMA) was obtained from Sartomer Company Inc., Singapore), cyclohexyl acrylate (CHMA) was obtained from Polysciences Inc., USA) and 1,4-butane diol diacrylate (BDDA) was obtained from Sartomer Company Inc., Singapore).

The separated curcumin from the preparative column chromatography procedure described above was weighed into a plastic vial. A solution of monomers containing 65.2% 2-phenoxy ethyl methacrylate (POEMA), 32.8% cyclohexyl acrylate (CHMA) and 2% 1,4-butane diol diacrylate (BDDA) by weight percentages respectively, was prepared and added to the curcumin-containing vial so as to give a curcumin concentration of approximately 0.1%. After dissolving the curcumin into the POEMA/CHMA/BDDA monomer solution, a catalytic amount (0.3%) of dilauroyl peroxide was added to the solution as a polymerization initiator.

Rod-shaped objects of 14 mm in diameter and of 100 mm in length were prepared from the polymeric mixture by placing the curcumin/monomer solution in vials and pressure fitting the closure by keeping the 'He' jacket over it. Polymerization was effected by placing the vials into 40° C. oven and curing for 24 hours. The temperature of the oven was raised to 60° C. and the vials were heated for 3 hours to effect the post cure of the rod stock. Circular slices were cut from the rods and subjected to Soxhlet extraction for 3 hours in toluene.

Thereafter the extracted material samples were dried in air followed by drying at about 50° C. under vacuum. The UV/Vis transmission and absorption spectra was measured for the sample slices before and after the Soxhlet extraction and drying.

Extraction is a typical step in IOL manufacturing processes, wherein the matrix is swelled with water to a certain limit (typically lower than 30% by weight) and the extractables are removed by various solvents. Curcuminoid compounds, according to some embodiments of the present invention, are entrapped in the matrix, however, their interaction with acrylic matrix is such that they do not leave the matrix even under extraction conditions.

Figure 2A:
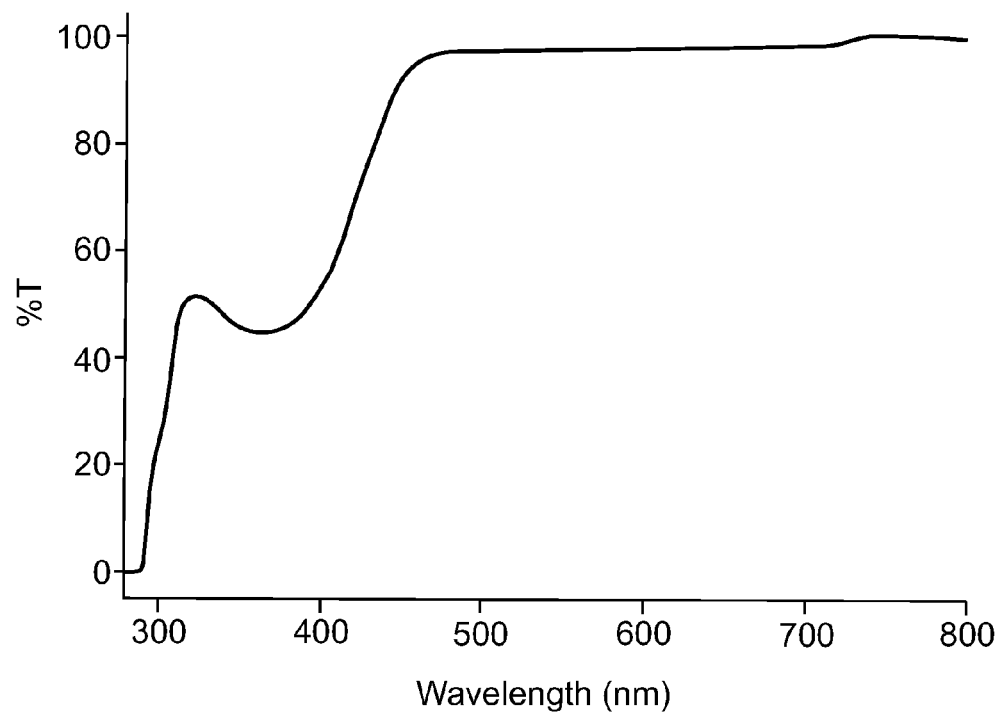
FIGS. 2A-B present the UV/Vis transmission and absorption spectra as measured from slice samples of a rod-shaped object prepared from a curcumin/POEMA/CHMA/BDDA polymerization mixture, an exemplary composition according to some embodiments of the present invention, after mild washing and drying (FIG. 2A) and after Soxhlet extraction for 3 hours in toluene (FIG. 2B)
Figure 2B:
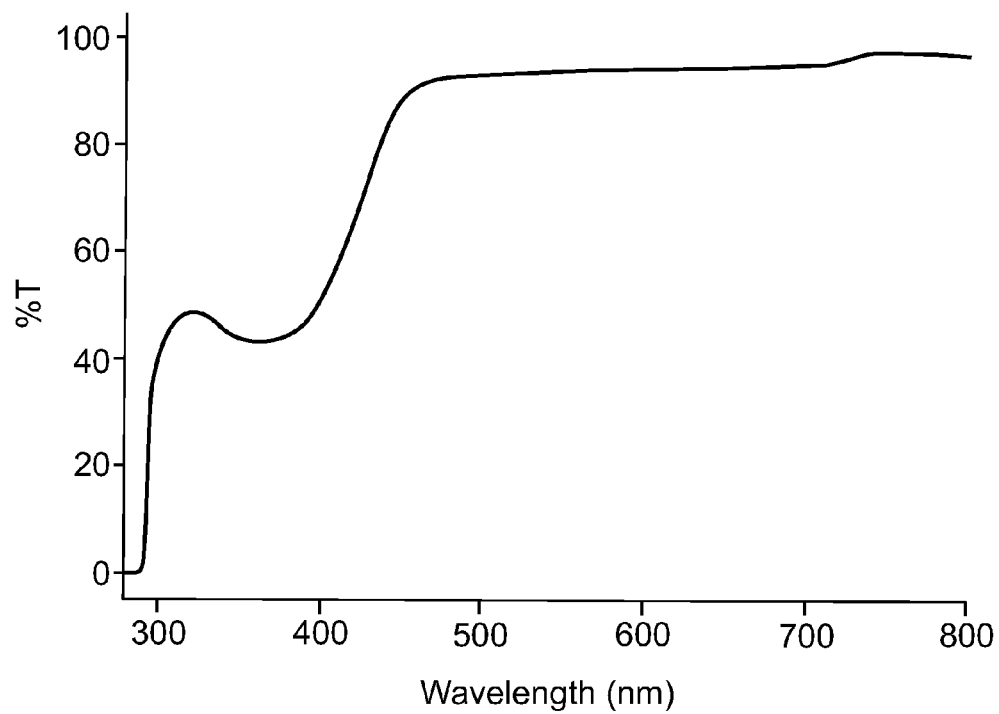

FIGS. 2A-B present the UV/Vis transmission and absorption spectra as measured from slice samples of the rod-shaped object prepared from the curcumin/POEMA/CHMA/BDDA polymerization mixture, an exemplary composition according to some embodiments of the present invention, after mild washing and drying (FIG. 2A) and after Soxhlet extraction for 3 hours in toluene (FIG. 2B).

As can be seen in FIGS. 2A-B, the spectra shows that UV light is blocked and the sample does not transmit UV light in a range of about 180 nm to 380 nm. As can further be seen in FIGS. 2A-B, the UV/VIS transmission and absorption spectra of the samples before and after Soxhlet extraction is remarkably similar, indicating no measurable leakage of curcumin from the sample during extraction.

These results affirm that curcumin is an effective UV stabilizing compound in a polymeric matrix. UVB and UVC light rays are substantially blocked up to 390 nm with transmittance of less than 50% ($\lambda$=392.5 nm; % T=49.65%) with about 0.025 percent by weight of curcumin from the total weight of the sample. The comparative spectra before and after Soxhlet extraction affirm that curcumin is an effective UV stabilizer as an entrapped species in an acrylic matrix, exhibiting no tendency of leaching out of the acrylic matrix even when it is subjected to the exhaustive extraction (transmittance at $\lambda$=378.5 nm is 45.918% before extraction, and 43.825% after extraction).

Example 8

UV-Blocking Strength Comparison

In order to evaluate the UV/Vis interaction attributes of the curcumin-doped transparent object, prepared as described hereinabove, these properties were compared with those obtained from a transparent object prepared with 4-[(E)-phenyldiazenyl]phenyl-2-methacrylate (PDPMA), a commercially available diphenyl azo compound. Curcumin and PDPMA were used at a concentration of 0.005 wt % and 0.25 wt % respectively.

A solution of monomers containing 65.2% POEMA, 32.8% CHMA and 2% BDDA (1,4-butane diol diacrylate) by weight respectively, was mixed to give the aforementioned test compound concentration. Thereafter, dilauroyl peroxide (0.3%) was added as a polymerization initiator.

Rod-shaped objects having 14 mm in diameter and of 100 mm in length were prepared as described hereinabove. Circular slices were cut from the rods and Soxhlet-extracted for 3 hours in toluene. Following the extraction, the material samples were dried in air followed by drying at about 50° C. under vacuum.

The dye's strength can be assessed by comparing transmittance values at various wavelengths in the visible blue light region of 400-500 nm (unlike curcumin, no commercially available synthetic yellow dye absorbs in UV region).

Figure 3A:
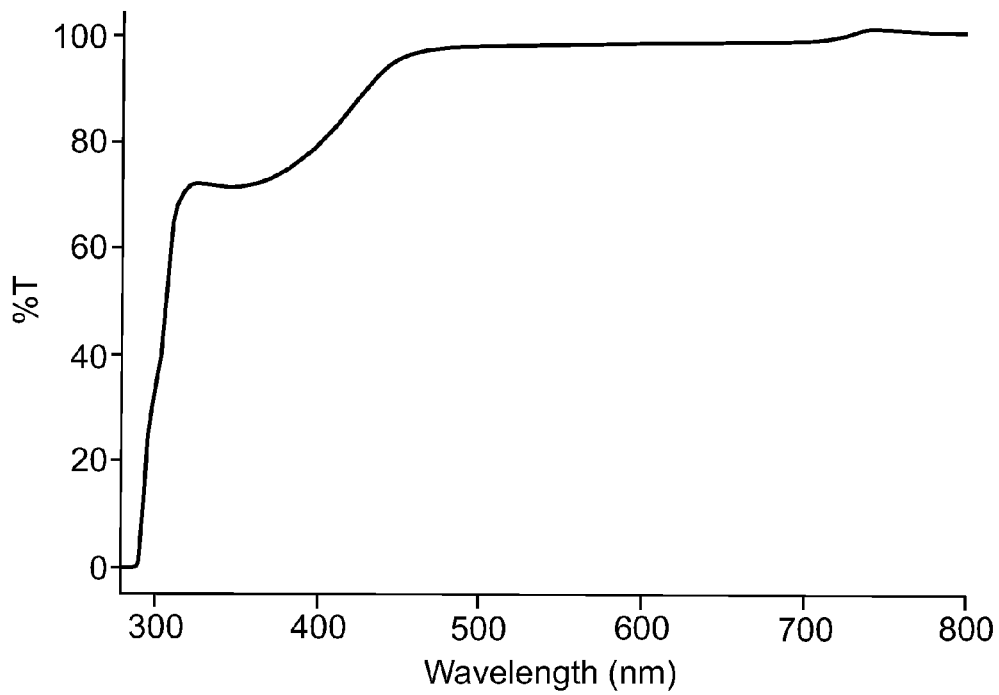
FIGS. 3A-D present the UV/Vis transmission and absorption spectra, as measured after Soxhlet extraction and drying, obtained from transparent slices having curcumin at a final content of 0.005 weight percents (FIG. 3A), PDPMA at a final content of 0.005 weight percents (FIG. 3B), curcumin at a final content of 0.025 weight percents (FIG. 3C), and PDPMA at a final content of 0.025 weight percents (FIG. 3D)
Figure 3B:
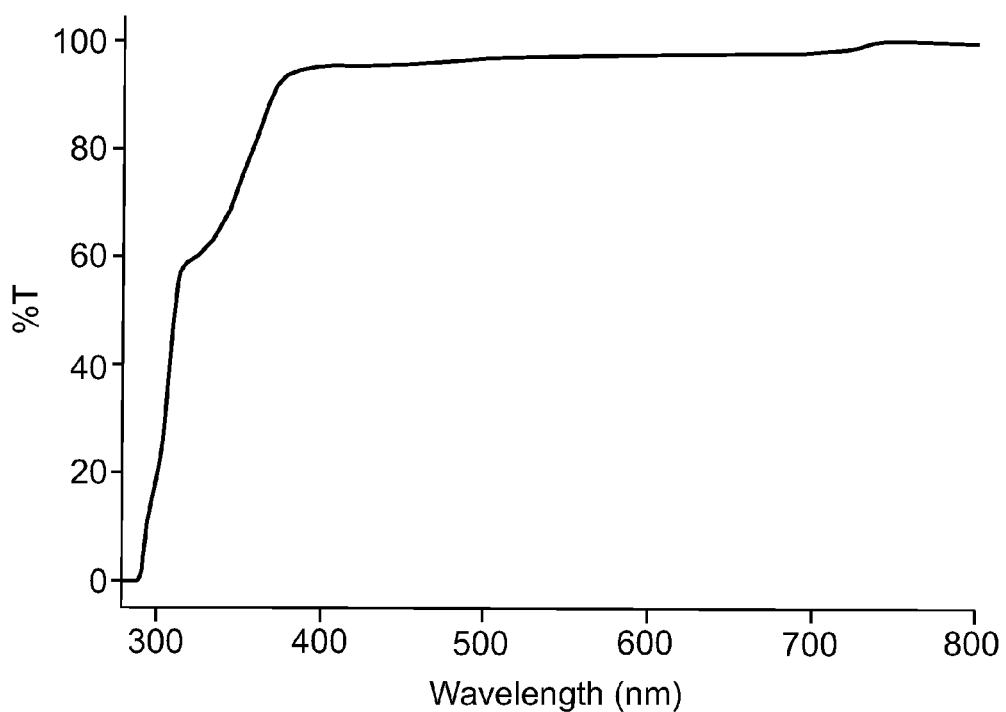
Figure 3C:
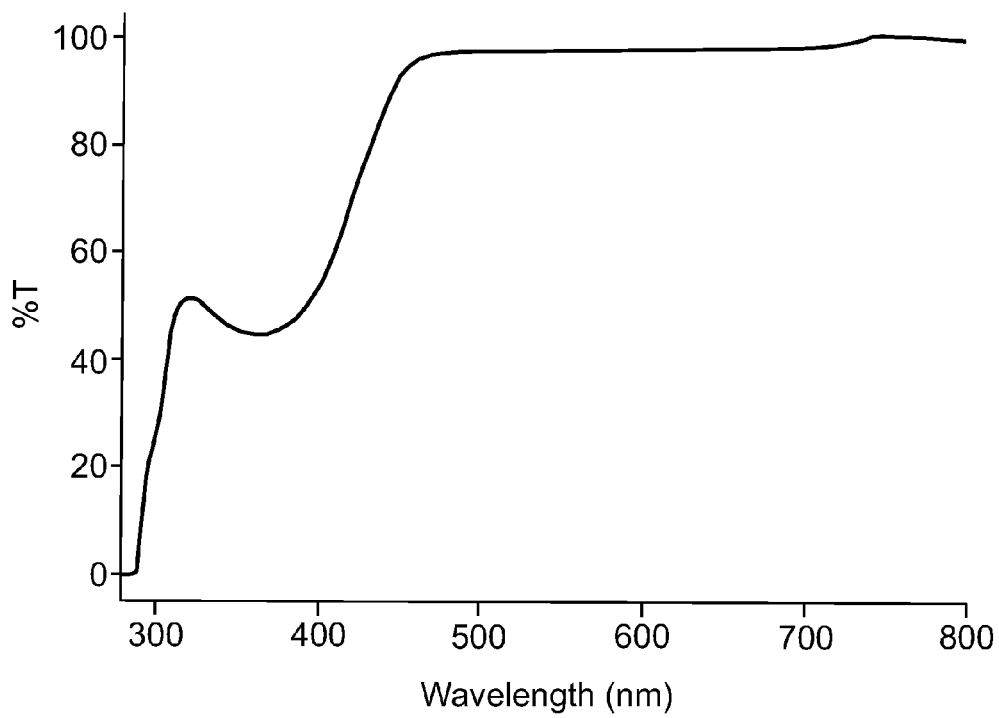
Figure 3D:
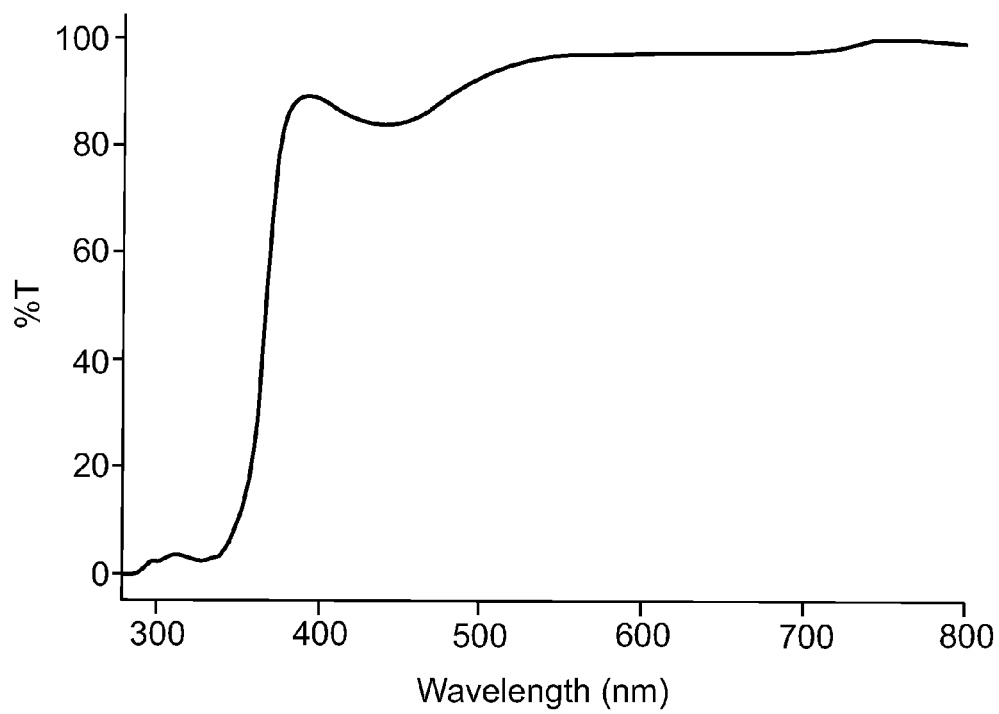

FIGS. 3A-D present the UV/Vis transmission and absorption spectra, measured after Soxhlet extraction and drying, obtained from transparent slices having curcumin at a final content of 0.005 weight percents (FIG. 3A), PDPMA at a final content of 0.005 weight percents (FIG. 3B), curcumin at a final content of 0.025 weight percents (FIG. 3C), and PDPMA at a final content of 0.025 weight percents (FIG. 3D).

As can be seen in FIGS. 3A-D, the UV-blocking strength of the transparent slices having curcumin as a UV-blocker additive, as estimated and compared by their transmission values at wavelengths in the visible blue light region (400-500 nm), are far more intensive than those having PDPMA. Specifically, transmittance at $\lambda$=430 nm is about 60% FIG. 3C, about 85% in FIG. 3D, indicating more synthetic dye amount is needed to partly block the visible blue light.

Hence, curcumin is a yellow dye exhibiting dual function by acting as a UV absorber and visible blue light blocker.

Example 9

UV-Blocker Strength Stability

Lens of 20 diopter with center thickness of 0.75 mm, optic diameter of 6 mm and an overall length of 12.5 mm were prepared from a solution of monomers containing 65.2% POEMA, 32.8% CHMA and 2% BDDA (1,4-butane diol diacrylate) by weight.

The tested curcuminoid compound was added to the monomers mixture to a final concentration of 0.025% w/w and 0.05% w/w, and thereafter dilauroyl peroxide (0.3%) was added as a polymerization initiator.

This pre-polymerization mixture was loaded into two PP mold halves and cured in an oven at 80° C. for 26 hours. Thereafter the molds were kept in a vacuum oven at 110° C. for 3 hours.

After curing, the cast product in the form of a thin circular disc was milled to the above mentioned dimensions and subjected to extraction treatment.

The amount of absorbance between 280-500 nm lost after Soxhlet extraction was used as an indication of the amount of curcumin removed from the lens material by the Soxhlet extraction process.

Figure 4A:
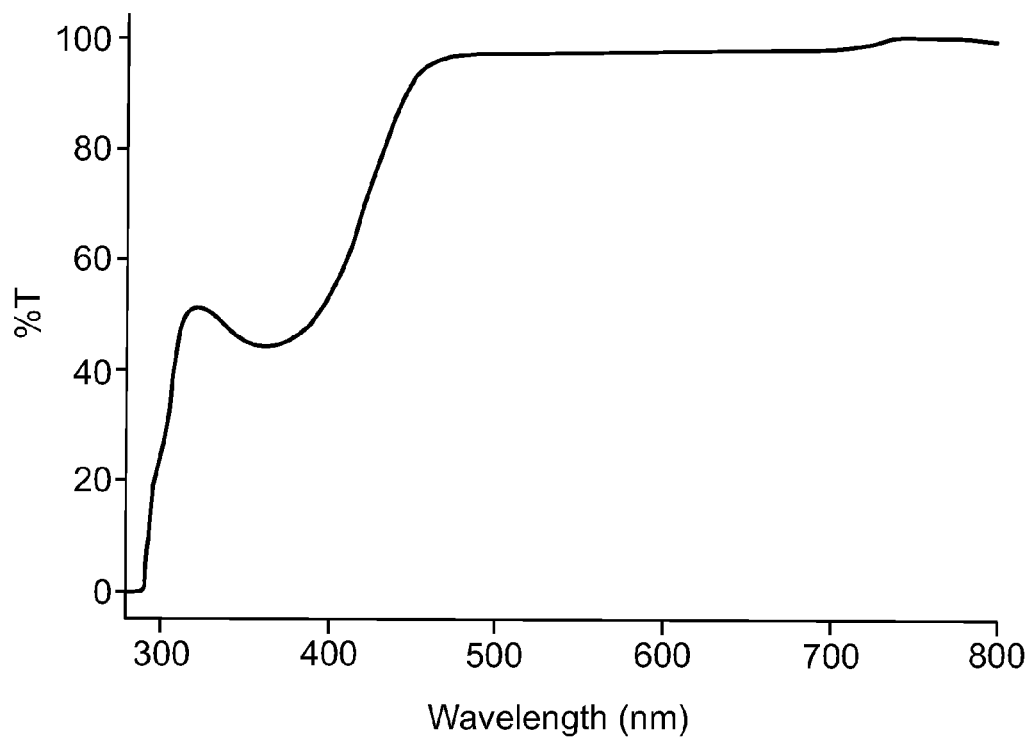
FIGS. 4A-D present the UV/Vis absorption spectra, as collected from lens prepared with curcumin at 0.025 weight percentage, before extraction (FIG. 4A), from the same lens after extraction (FIG. 4B), from lens prepared with curcumin at 0.05 weight percentage, before extraction (FIG. 4C), and from the latter lens after extraction (FIG. 4D).
Figure 4B:
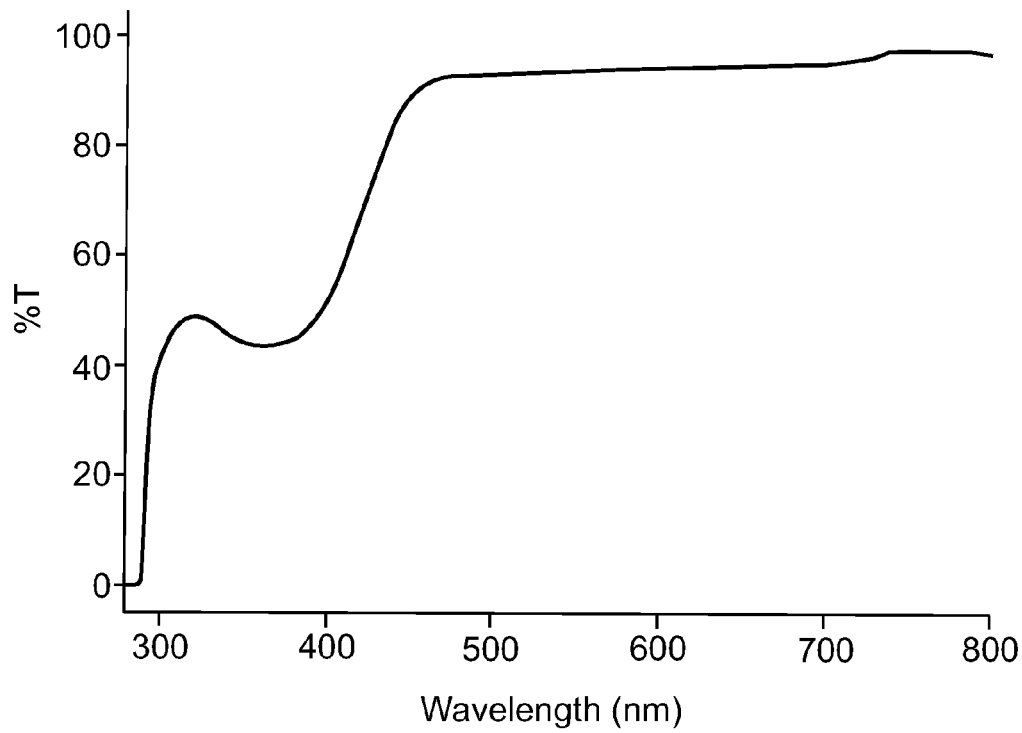
Figure 4C:
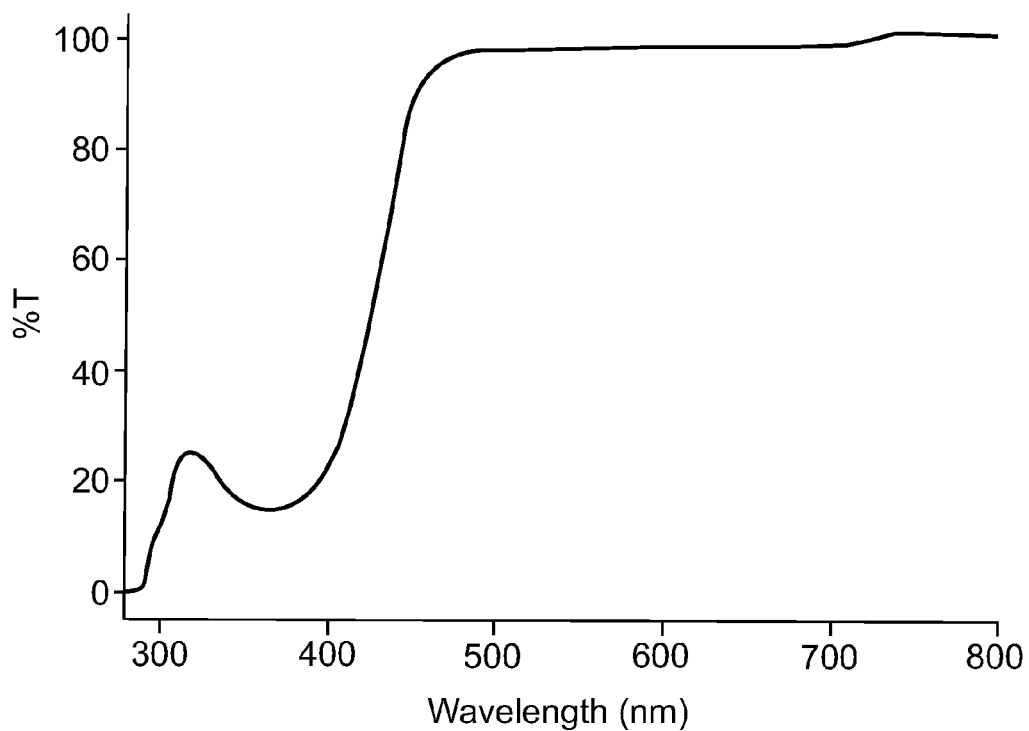
Figure 4D:
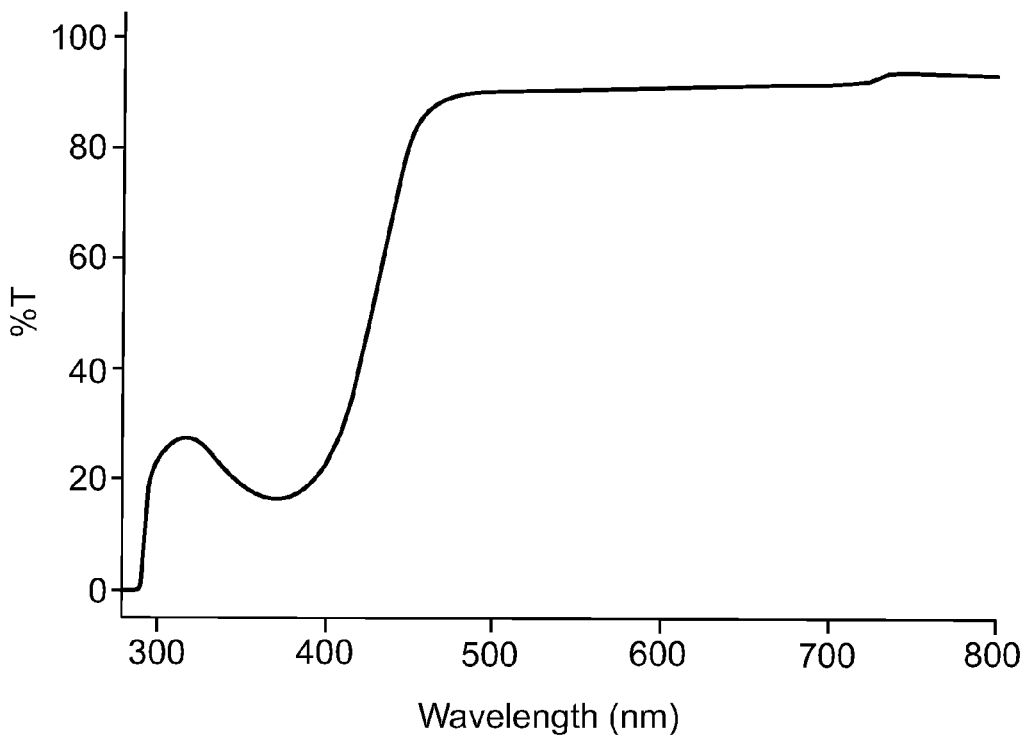

FIGS. 4A-D present the UV/Vis absorption spectra, as collected from lens before extraction prepared with curcumin at 0.025 weight percentage (FIG. 4A), from the same lens after extraction (FIG. 4B), from lens before extraction prepared with curcumin at 0.05 weight percentage (FIG. 4C), and from the latter lens after extraction (FIG. 4D).

As can be seen in FIGS. 4A-D, the low decrease in absorbance at wavelength range between 280 nm to 500 nm indicated that very small amount of curcumin leach out of the lens during exhaustive solvent extraction. Apart from UV blocking, it is evident that curcumin remains entrapped in the acrylic matrix in spite of subjecting the lens to intense extracting conditions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A co-polymeric composition comprising a polymeric backbone composed of a plurality of backbone units covalently linked to one another, said backbone units being derived from a pre-polymerization mixture of monomers which comprises:
    a first aromatic acrylate monomer, characterized as forming a first homopolymer having a refractive index that ranges from 1.50 to 1.53;
    a second aromatic acrylate monomer, characterized as forming a second homopolymer having a Tg lower by a range of 2° C. to 30° C. than a Tg of said first homopolymer;
    a third monomer, characterized as forming a third homopolymer having a Tg lower than 35° C.;
    a fourth monomer, characterized as forming a fourth homopolymer which is capable of absorbing water to at least 20% of the total weight of said fourth homopolymer; and
    a fifth monomer, being a crosslinking monomer, wherein:
    a concentration of said first aromatic acrylate monomer ranges from 50% to 60% of the total weight of the composition;
    a concentration of said second aromatic acrylate monomer ranges from 15% to 20% of the total weight of the composition;
    a concentration of said third monomer ranges from 10% to 15% of the total weight of the composition;
    a concentration of said fourth monomer ranges from 5% to 10% of the total weight of the composition;
    a concentration of said fifth monomer ranges from 2% to 5% of the total weight of the composition; and
    the composition is characterized by a glass transition temperature not higher than 5° C. and being formulated for ophthalmic application, wherein the composition is characterized by at least one of: a loop pull force mechanical strength of at least 60 grams; a Shore A hardness that ranges from 77 to 80; and an unfolding time of less than 6 seconds.

2. The composition of claim 1, further comprising an ultraviolet absorbing compound.

3. The composition of claim 1, wherein:
    a concentration of said first aromatic acrylate monomer ranges from 52% to 59% of the total weight of the composition;
    said concentration of said second aromatic acrylate monomer ranges from 15% to 19% of the total weight of the composition;
    said concentration of said third monomer ranges from 11% to 15% of the total weight of the composition;
    said concentration of said fourth monomer ranges from 7% to 9% of the total weight of the composition; and
    said concentration of said fifth monomer ranges from 2% to 3.5% of the total weight of the composition.

4. The composition of claim 1, wherein said mixture further comprises a free radical polymerization initiator.

5. The composition of claim 1, wherein said mixture further comprises a curing agent.

6. The composition of claim 1, further comprising at least one curcuminoid compound incorporated therein or thereon.

7. The composition of claim 6, wherein a concentration of said curcuminoid compound ranges from 0.0002 weight percentage to 1 weight percentage of the total weight of the composition.

8. The composition of claim 7, wherein said concentration of said curcuminoid compound decreases by less than 0.0001 weight percentage when the composition is subjected to a solvent extraction.

9. A process of preparing the composition of claim 1, the process comprising:
    admixing said pre-polymerization mixture of monomers and a free radical polymerization initiator;
    heating said pre-polymerization mixture to 40° C. while stirring until a viscosity reach 120 cps at 25° C.;
    degassing said pre-polymerization mixture so as remove volatile residues;
    admixing an additional amount of said initiator into said pre-polymerization mixture so as to obtain a reaction mixture;
    admixing a curing agent into said reaction mixture;
    casting said reaction mixture into a mold; and
    exposing said reaction mixture to curing conditions, to thereby obtain the composition.

10. The process of claim 9, further comprising, subsequent to said exposing said reaction mixture to said curing conditions:
    subjecting the composition to a multiple extraction.

11. An ophthalmic or ocular device, comprising the composition of claim 1.

12. The ophthalmic or ocular device of claim 11, selected from the group consisting of an intraocular lens (IOL), a contact lens, an implantable ocular device, a keratoprosthesis, a phakic lens, an aphakic lens, a corneal ring, a capsular bag extension ring, a corneal inlay and a corneal onlay.

13. A co-polymeric composition comprising a polymeric backbone composed of a plurality of backbone units covalently linked to one another and a curcuminoid compound incorporated in or on the composition, said backbone units being derived from a pre-polymerization mixture of monomers which comprises:
   a first aromatic acrylate monomer, characterized as forming a first homopolymer having a refractive index that ranges from 1.50 to 1.53;
   a second aromatic acrylate monomer, characterized as forming a second homopolymer having a Tg lower by a range of 2° C. to 30° C. than a Tg of said first homopolymer;
   a third monomer, characterized as forming a third homopolymer having a Tg lower than 35° C.;
   a fourth monomer, characterized as forming a fourth homopolymer which is capable of absorbing water to at least 20% of the total weight of said fourth homopolymer; and
   a fifth monomer, being a crosslinking monomer,
   wherein:
   a concentration of said first aromatic acrylate monomer ranges from 50% to 60% of the total weight of the composition;
   a concentration of said second aromatic acrylate monomer ranges from 15% to 20% of the total weight of the composition;
   a concentration of said third monomer ranges from 10% to 15% of the total weight of the composition;
   a concentration of said fourth monomer ranges from 5% to 10% of the total weight of the composition;
   a concentration of said fifth monomer ranges from 2% to 5% of the total weight of the composition; and
   the composition is characterized by a glass transition temperature not higher than 5° C. and being formulated for ophthalmic application, wherein the composition is characterized by at least one of: a loop pull force mechanical strength of at least 60 grams; a Shore A hardness that ranges from 77 to 80; and an unfolding time of less than 6 seconds.

14. The composition of claim 13, wherein:
   a concentration of said first aromatic acrylate monomer ranges from 52% to 59% of the total weight of the composition;
   said concentration of said second aromatic acrylate monomer ranges from 15% to 19% of the total weight of the composition;
   said concentration of said third monomer ranges from 11% to 15% of the total weight of the composition;
   said concentration of said fourth monomer ranges from 7% to 9% of the total weight of the composition; and
   said concentration of said fifth monomer ranges from 2% to 3.5% of the total weight of the composition.

15. The composition of claim 13, wherein said mixture further comprises a free radical polymerization initiator.

16. The composition of claim 13, wherein said mixture further comprises a curing agent.

17. The composition of claim 13, having a visible light transmission of at least 97% of incident visible light.

18. The composition of claim 13, having a refractive index of at least 1.53.

19. The composition of claim 13, having loop pull force mechanical strength of at least 60 grams.

20. The composition of claim 13, characterized by Shore A hardness that ranges from 77 to 80.

21. The composition of claim 13, having an unfolding time of less than 6 seconds.

22. The composition of claim 13, having a leachable content of less than 0.6%.

23. The composition of claim 13, wherein a concentration of said curcuminoid compound ranges from 0.0002 weight percentage to 1 weight percentage of the total weight of the composition.

24. The composition of claim 23, wherein said concentration of said curcuminoid compound decreases by less than 0.0001 weight percentage when the composition is subjected to a solvent extraction.

25. An ophthalmic or ocular device, comprising the composition of claim 13.

26. The device of claim 25, selected from the group consisting of an intraocular lens (IOL), a contact lens, an implantable ocular device, a keratoprosthesis, a phakic lens, an aphakic lens, a corneal ring, a capsular bag extension ring, a corneal inlay and a corneal onlay.

27. The composition of claim 13, further characterized by at least one of:
   a visible light transmission of at least 97% of incident visible light; and
   a refractive index of at least 1.53.

* * * * *

UNITED STATES PATENT AND TRADEMARK OFFICE
CERTIFICATE OF CORRECTION

PATENT NO. : 9,622,853 B2
APPLICATION NO. : 13/808614
DATED : April 18, 2017
INVENTOR(S) : Sanjay Ram Swaroop Argal et al.

It is certified that error appears in the above-identified patent and that said Letters Patent is hereby corrected as shown below:

On the Title Page

Insert the following:
Item -- (30) Foreign Application Priority Data
Feb. 1, 2011   (IN)................ 273/MUM/2011
Oct. 18, 2010  (IN)................ 2888/MUM/2010
Jul. 5, 2010   (IN)................ 1938/MUM/2010 --

Signed and Sealed this
Twenty-sixth Day of December, 2017

Joseph Matal
*Performing the Functions and Duties of the
Under Secretary of Commerce for Intellectual Property and
Director of the United States Patent and Trademark Office*